US012582430B2

(12) United States Patent
Kovac et al.

(10) Patent No.: US 12,582,430 B2
(45) Date of Patent: Mar. 24, 2026

(54) NEGATIVE PRESSURE-BASED GRIPPING SYSTEM AND METHOD

(71) Applicant: Septulus AB, Lund (SE)

(72) Inventors: Tim Kovac, Anderslöv (SE); Henrik Bjursten, Lund (SE); Matthias Gotberg, Lund (SE); Magnus Dencker, Höllviken (SE)

(73) Assignee: Septulus AB, Lund (SE)

( * ) Notice: Subject to any disclaimer, the term of this patent is extended or adjusted under 35 U.S.C. 154(b) by 1328 days.

(21) Appl. No.: 16/967,646

(22) PCT Filed: Feb. 6, 2019

(86) PCT No.: PCT/EP2019/052893
§ 371 (c)(1),
(2) Date: Aug. 5, 2020

(87) PCT Pub. No.: WO2019/154847
PCT Pub. Date: Aug. 15, 2019

(65) Prior Publication Data
US 2021/0085353 A1     Mar. 25, 2021

(30) Foreign Application Priority Data
Feb. 6, 2018    (EP) ..................................... 18155266

(51) Int. Cl.
*A61B 17/04*          (2006.01)
*A61B 17/068*         (2006.01)
(Continued)

(52) U.S. Cl.
CPC .......... *A61B 17/30* (2013.01); *A61B 17/0469* (2013.01); *A61B 17/068* (2013.01);
(Continued)

(58) Field of Classification Search
CPC .............. A61B 17/0469; A61B 17/068; A61B 2017/0243; A61B 2017/0409;
(Continued)

(56) References Cited

U.S. PATENT DOCUMENTS 5,443,446 A      8/1995   Shturman
6,478,029 B1 *  11/2002   Boyd ..................... A61B 90/36
                                                          128/898
(Continued)

FOREIGN PATENT DOCUMENTS

CN         1198664 A      11/1998
JP      2011510786 A       4/2011
(Continued)

OTHER PUBLICATIONS

Matos J, Kronzon I, Panagopoulos G, Perk G.. Mitral Annular Plane Systolic Excursion as a Surrogate for Left Ventricular Ejection Fraction. Journal of the American Society of Echocardiography , vol. 25 , Issue 9 , 969-974.
(Continued)

*Primary Examiner* — Elizabeth Houston
*Assistant Examiner* — Jonathan A Hollm
(74) *Attorney, Agent, or Firm* — Dinsmore & Shohl LLP

(57)          ABSTRACT

The present disclosure relates to negative pressure-based gripping system for gripping and retaining a target, preferably a moving target, such as a heart of a human or animal, in a fixed position, comprising: a catheter having a tubular body; a proximal end; and a remotely operable and flexible distal end section with a distal opening; a negative pressure generator, such as a vacuum pump, in connection with the tubular body; and a control unit configured to position the distal end of the catheter, wherein said control unit is further configured to control an operation of the negative pressure generator such that a negative pressure is generated in the
(Continued)

tubular body to grip the target by the distal opening of the catheter upon positioning of the distal opening adjacent to the target. The disclosure further relates to method for gripping and retaining a target, preferably a moving target, such as a heart of a human or animal, in a fixed position in relation to the device.

20 Claims, 15 Drawing Sheets

(51) Int. Cl.
| | |
|---|---|
| *A61B 17/30* | (2006.01) |
| *A61B 17/00* | (2006.01) |
| *A61B 17/02* | (2006.01) |
| *A61B 17/064* | (2006.01) |
| *A61B 90/00* | (2016.01) |

(52) U.S. Cl.
CPC .............. *A61B 2017/00292* (2013.01); *A61B 2017/0243* (2013.01); *A61B 2017/0409* (2013.01); *A61B 2017/0441* (2013.01); *A61B 2017/0649* (2013.01); *A61B 2017/306* (2013.01); *A61B 2090/064* (2016.02); *A61B 2217/005* (2013.01)

(58) Field of Classification Search
CPC .... A61B 2017/0441; A61B 2017/0649; A61B 2017/306; A61B 2217/005
See application file for complete search history.

(56) References Cited

U.S. PATENT DOCUMENTS

| | | | | |
|---|---|---|---|---|
| 6,602,183 | B1 * | 8/2003 | Levi ........................ | A61B 17/02 |
| | | | | 600/37 |
| 9,877,833 | B1 * | 1/2018 | Bishop .................... | A61B 17/08 |
| 10,610,249 | B2 | 4/2020 | Bjursten | |
| 2007/0038293 | A1 | 2/2007 | St.Goar et al. | |
| 2009/0054803 | A1 * | 2/2009 | Saadat ............... | A61B 17/3423 |
| | | | | 600/546 |
| 2010/0004506 | A1 | 1/2010 | Saadat | |
| 2010/0185044 | A1 * | 7/2010 | Kassab ................. | A61M 25/04 |
| | | | | 600/16 |
| 2011/0213459 | A1 * | 9/2011 | Garrison .......... | A61B 17/12122 |
| | | | | 623/2.11 |
| 2013/0218192 | A1 | 8/2013 | Erzberger et al. | |
| 2014/0163652 | A1 | 6/2014 | Witzel et al. | |
| 2015/0066016 | A1 | 3/2015 | Miles et al. | |
| 2015/0173794 | A1 | 6/2015 | Kurth et al. | |
| 2017/0035434 | A1 | 2/2017 | Forbes | |

FOREIGN PATENT DOCUMENTS

| | | |
|---|---|---|
| JP | 2016027905 A | 2/2016 |
| JP | 2017519536 A | 7/2017 |
| WO | 2012040865 A1 | 4/2012 |

OTHER PUBLICATIONS

Arnoczky SP, Aksan A. Thermal modification of connective tissues: Basic science considerations and clinical Implications. J Am Acad Orthop Surg 2000;8:305-313.
Goel R, Witzel T, Dickens D, Takeda PA, and Heuser RR. (2009), The QuantumCor device for treating mitral regurgitation: An animal study. Cathet. Cardiovasc. Intervent., 74: 43-48.
Heuser RR, Witzel T, Dickens D, Takeda PA. Percutaneous treatment for mitral regurgitation: the QuantumCor system. J Interv Cardiol 2008;21:178-82.

Murarka S, Witzel T, Dickens D, Takeda PA, and Heuser RR. (2009), Collagen Mechanics: A Rationale for Radiofrequency Energy to Treat Mitral Regurgitaton. Journal of Interventional Cardiology, 22: 184-190.
Wall MS, Deng XH, Torzilli PA, Doty SB, O'Brien SJ, Warren RF. Thermal modification of collagen. J Shoulder Elbow Surg 1999;8:339-344.
Alkadhi H, Desbiolles L, Stolzmann P, Leschka S, Scheffel H, Plass A, Schertler T, Trindade PT, Genoni M, Cattin P, Marincek B, Frauenfelder T. Mitral annular shape, size, and motion in normals and in patients with cardiomyopathy: evaluation with computed tomography. Invest Radiol. Apr. 2009;44(4):218-25.
Braun, Jerry, et al. "Restrictive mitral annuloplasty cures ischemic mitral regurgitation and heart failure." The Annals of thoracic surgery 85.2 (2008): 430-437.
Yiu, Siu F., et al. "Determinants of the degree of functional mitral regurgitation in patients with systolic left ventricular dysfunction." Circulation 102.12 (2000): 1400-1406.
He, Shengqiu, et al. "Integrated mechanism for functional mitral regurgitation." Circulation 96.6 (1997): 1826-1834.
Lancellotti, Patrizio, Paul L. Gérard, and Luc A. Piérard. "Long-term outcome of patients with heart failure and dynamic functional mitral regurgitation." European heart journal 26.15 (2005): 1528-1532.
Perier, Patrick, et al. "Toward a new paradigm for the reconstruction of posterior leaflet prolapse: midterm results of the 'respect rather than resect" approach. The Annals of thoracic surgery 86.3 (2008): 718-725.
Devereux, Richard B., et al. "Mitral valve prolapse." Circulation 54.1 (1976): 3-14.
Hayek, Emil, Christian N. Gring, and Brian P. Griffin. "Mitral valve prolapse." The Lancet 365.9458 (2005): 507-518.
Adams, David H., Raphael Rosenhek, and Volkmar Falk. "Degenerative mitral valve regurgitation: best practice revolution." European heart journal 31.16 (2010): 1958-1966.
Daoud, Emile G., Steven J. Kalbfletsch, and John D. Hummel. "Intracardiac echocardiography to guide transseptal left heart catheterization for radiofrequency catheter ablation." Journal of cardiovascular electrophysiology 10.3 (1999): 358-363.
Earley, Mark J. "How to perform a transseptal puncture." Heart 95.1 (2009): 85-92.
Wolf PA, Abbott RD, Kannel WB. Atrial Fibrillation: A Major Contributor to Stroke in the Elderly The Framingham Study. Arch Intern Med. 1987;147(9):1561-1564. doi:10.1001/archinte.1987. 00370090041008.
Holmes, David R., et al. "Prospective randomized evaluation of the Watchman Left Atrial Appendage Closure device in patients with atrial fibrillation versus long-term warfarin therapy: the PREVAIL trial." Journal of the American College of Cardiology 64.1 (2014): 1-12.
Reddy, Vivek Y., et al. "Left atrial appendage closure with the Watchman device in patients with a contraindication for oral anticoagulation: the ASAP study (ASA Plavix Feasibility Study With Watchman Left Atrial Appendage Closure Technology)." Journal of the American College of Cardiology 61.25 (2013): 2551-2556.
Meier, Bernhard, et al. "Transcatheter left atrial appendage occlusion with Amplatzer devices to obviate anticoagulation in patients with atrial fibrillation." Catheterization and cardiovascular interventions 60.3 (2003): 417-422.
Freixa, Xavier, et al. "Left atrial appendage occlusion: initial experience with the Amplatzer™ Amulet™." International journal of cardiology 174.3 (2014): 492-496.
Tang, Gilbert HL, et al. "Tricuspid valve repair with an annuloplasty ring results in improved long-term outcomes." Circulation 114.1 suppl (2006): I-577.
International Search Report dated Apr. 5, 2019; International Application No. PCT/EP2019/052893.

* cited by examiner

NEGATIVE PRESSURE-BASED GRIPPING SYSTEM AND METHOD

CROSS-REFERENCE TO RELATED APPLICATIONS

This application is the U.S. national stage of PCT/EP2019/052893 filed Feb. 6, 2019, which claims priority to European Patent Application No. 18155266.2, filed Feb. 6, 2018, the entire content of both are incorporated herein by reference in their entirety.

FIELD OF THE INVENTION

The present disclosure relates to a negative pressure-based gripping system for gripping and retaining a target and a method for gripping and retaining a target, preferably a moving target, such as a heart of a human or animal, in a fixed position in relation to a device. The disclosure further relates to suture fastening, injection and mitral valve chordal repair devices based on the negative pressure-based gripping system, as well as a method for gripping and retaining a target and for performing mitral valve chordal repair of a heart.

BACKGROUND OF THE INVENTION

Heart disease is the most common chronic disease in the developed world, and quickly increasing the developing world. It is responsible for 16% of the deaths in high income countries and 14% in middle income countries as defined by the World Health Organization. Among the heart conditions, Ischemic heart disease is the most common cause of mortality, with valvular disease in the second place. Between 2% and 4% of the population over 65 is estimated to have some type of valvular disease. The most common valvular disease is the aortic stenosis, followed by mitral stenosis and mitral regurgitation. The other valves of the heart can also be affected by disease, where tricuspid and pulmonary regurgitation are not uncommon. Another type of heart disease is rhythm disturbances, where the regular heart rhythm is disturbed and either is beating too slow, too quick or irregularly. The most common type of arrhythmia is the irregular and fast type called atrial fibrillation, which has been estimated to affect 33 million persons worldwide. This irregular heart rhythm often leads to formation of blood clots in the hearts, which can travel with the blood and occlude an artery. If this happens in the brain, the person will suffer a stroke, and therefore atrial fibrillation a dangerous disease.

Various types of treatments and surgical procedures (including, for example, coronary revascularization, pacemaker therapy, mitral annuloplasty, mitral leaflet-plasty, mitral valve replacement, replacement of ruptured chordae, steps of transseptal puncture, aortic valve replacement, tricuspid valve plasty, tricuspid valve replacement, pulmonary valve replacement, septal reduction therapy, surgical myectomi etc.) require open heart surgery to warrant a successful procedure. Open heart surgical procedures are invasive and often involve discomfort, substantial risks, and prolonged convalescence for the patent undergoing the surgery. Normally open-heart surgery is performed with the help of heart-lung machine that will make it possible to arrest the heart while the procedure is performed. By arresting the heart, the surgeon will not only have an organ that is still but it also gives access to the inside of the heart.

Some cardiac surgical procedures require the surgeon to perform operations on moving organs or tissue within the human body. A beating human heart is one example of an organ that may require very precise and sometimes complex surgery and treatment while the heart is moving. Performing such operations on a beating heart is obviously even more difficult. For this reason there have been attempts to stabilize the heart in order to facilitate the work of the surgeon. For example, there are a number of mechanical arms, holders, positioners for holding a beating heart in a fixed position during surgery.

SUMMARY OF INVENTION

The present disclosure relates to a negative pressure-based gripping system for gripping and retaining a target, preferably a moving target, such as a heart of a human or animal, in a fixed position, comprising:

- a catheter having a tubular body; a proximal end; and a remotely operable and flexible distal end section with at least one distal opening;
- a negative pressure generator, such as a vacuum pump or fluid pump or pump motor, in connection with the tubular body; and
- a control unit configured to position the distal end of the catheter, wherein said control unit is further configured to control an operation of the negative pressure generator such that a negative pressure is generated in the tubular body to grip the target by the at least one distal opening of the catheter upon positioning of the at least one distal opening adjacent to the target.

Preferably the catheter is a flexible catheter that is arranged to be introduced by a transfemoral, transjugular, transaortic, transcaval, transapical, or subclavian access to the heart. The system may thereby be used less invasively in the sense that open heart cardiac surgical procedures can be avoided. Preferably, the negative pressure-based gripping system is arranged to operate inside a heart. In such a configuration the distal opening of the catheter can be positioned adjacent to the target (e.g. a human heart), and upon gripping of the target by means of the negative pressure generation, the device can puncture tissue and be introduced to operate on the inside of the target. The present system is able to assist operation directly on a beating heart. By having a relatively small and thin catheter and remotely operable distal section it is possible to operate less invasively from the outside, for example, by inserting the catheter through the femoral vein or artery. Preferably the distal section is remotely operable and precisely steerable by means of a computer-assisted control and/or a mechanism in the handle of the device, and preferably the distal end can be tracked in real-time by, for example, imaging modalities. The distal section may therefore either be directly tracked by an ultrasound or x-ray based imaging system, or, alternatively, be further equipped with elements for signaling its position to a control system.

The inventors have moreover realized that if an operation is carried out on the target when the negative pressure-based gripping device is locked to the target by the negative pressure function, it may be acceptable that the heart is not fully stabilized in relation to the body or surrounding body parts/structures as long as the distal tip of the catheter can be stabilized relative to the tissue targeted for a procedural step, and the desired relation between tissue and device can be maintained in a dynamic environment.

According to one embodiment of the presently disclosed gripping system the negative pressure-based device is therefore fixed in relation to the heart to achieve this procedural advantage. The remotely operable and flexible distal end section may be locked in a rigid configuration in order to apply traction to or stabilize a specific region of tissue whereas the rest of the catheter can be made flexible. For this purpose, the remotely operable and flexible distal end section may comprise tendons for controlling movement of the distal end, preferably wherein the tendons extend along from the tubular body along the distal end section.

The control unit, itself, may be included in the system as a separate unit from the catheter, may be integrated into the proximal handle of the catheter, or integrated into the entire catheter and handle device structure. In these later integrated forms, control switches, pressure data from sensors, signal processing, feedback and warnings to the user, and fluid and negative pressure control, such as valve function, are included in the proximal handle and catheter elements of the device. For example, control buttons and data processing chips may be integrated into the handle, and valve function and warning lights may be included in the catheter.

When operating with the device close to or in a beating heart it may be a challenging task to position the distal opening sufficiently close to the target. As a consequence, when the negative pressure is generated in the tubular body to grip the target it is possible that the opening does not achieve grip on the intended tissue. Therefore, the device preferably comprises a pressure sensor for measuring a pressure in the catheter. The control unit for positioning the distal end may then be further configured to control the operation such that the negative pressure is disconnected or disabled if the measured pressure in the flexible catheter does not remain below a predetermined pressure threshold for a predetermined period of time to limit the amount of blood that is aspirated during the procedure. In order to further decrease the risk of blood loss, the system may further comprise a flush container for carrying a fluid suitable for being transferred into the human or animal, wherein said container is connected to the tubular body of the flexible catheter. After performing a gripping step, either successful or unsuccessful, blood drawn into the catheter and negative pressure system may be pushed or flushed back into the patient. Preferably the control unit then controls this functionality, which may be achieved by, for example, a connection to the tubular catheter, wherein an electrical motor or valve pump controlled by the control unit controls the flushing process.

The present disclosure further relates to a method for gripping and retaining a target, preferably a moving target, such as a heart or heart tissue of a human or animal, in a fixed position in relation to a device, comprising the steps of:
  providing a device having a catheter having a tubular body; a proximal end; and a remotely operable and flexible end section with a distal opening;
  positioning the distal opening adjacent to the target by steering the distal end remotely;
  generating a negative pressure in the tubular body;
  measuring the pressure in the tubular body for a predefined period of time;
  if the measured pressure remains below a predefined pressure threshold for longer than a predefined period of time, maintaining the negative pressure in the tubular body to retain the target, otherwise disabling the negative pressure.

Targets may also comprise other tissues and may also comprise a heart that is not beating.

The present disclosure further relates to a device and a method for gripping and retaining a target, preferably a moving target, such as a heart or heart tissue of a human or animal, in a fixed position in relation to a device while positioning, gripping and retaining at least one additional target (or a second position of the same target) with a negative pressure gripping mechanism of the same device or a related device at a next fixed position relative to the device. The procedure of gripping additional targets relative to the first may then be repeated at least once to incrementally move the grip position to a next target in a controlled and determined manner. In one embodiment the negative pressure-based gripping system comprises at least two individually controlled negative pressure gripping mechanisms comprising a remotely operable and flexible distal end section with a distal opening. The negative pressure-based gripping system may be configured to perform the steps of:
  for a first negative pressure gripping mechanism, positioning a first distal opening adjacent to the target at a first position by steering the distal end remotely;
  generating a negative pressure in the tubular body;
  measuring the pressure in the tubular body for a predefined period of time;
  if the measured pressure remains below a predefined pressure threshold for longer than a predefined period of time, maintaining the negative pressure in the tubular body to retain the target, otherwise disabling the negative pressure,
  repeating the gripping procedure for a second negative pressure gripping mechanism comprising a remotely operable and flexible distal end section with a distal opening, on a second position on the target.

Alternatively, an anchor, for example, a microforcep, fastener or screw may be used to attach the catheter to the first position and then move the first distal opening to the second position. By using this device and/or method the device can be moved from one position to another. By alternating and repeating the positioning and gripping of the first and second negative pressure gripping mechanisms it is possible to move the device (by "walking") over or along and area of the target in a very controlled manner.

The method may be carried out using any embodiment of the presently disclosed negative pressure-based gripping device and system. In particular the device may, in a first step, be introduced transfemorally to access the heart of a human or animal.

These and other aspects of the invention are set forth in the following detailed description if the invention.

DETAILED DESCRIPTION OF THE INVENTION

The present disclosure relates to a catheter having a tubular body; a proximal end; and a remotely operable and flexible distal end section with a distal opening. In a preferred embodiment the catheter is provided in the form of a negative pressure-based gripping system for gripping and retaining a target, preferably a moving target, such as a heart of a human or animal, in a fixed position. The catheter may be arranged to be connected to a negative pressure generator, such as a vacuum pump, fluid pump, or pump motor. The negative pressure generator is typically connected to the proximal end of the tubular body. The flexible distal end section is remotely operable, preferably by a control unit configured to position the distal end of the catheter. The control unit may be further configured to control an operation of the negative pressure generator such that a negative pressure is generated in the tubular body to grip the target by the distal opening of the catheter upon positioning of the distal opening adjacent to the target. Any reference to features belonging to the catheter may be seen as features related to either the catheter alone or the negative pressure-based gripping system. As will be understood by the person skilled in the art, some of the features described in the present disclosure are not strictly related to negative pressure-based gripping system.

Figure 13:
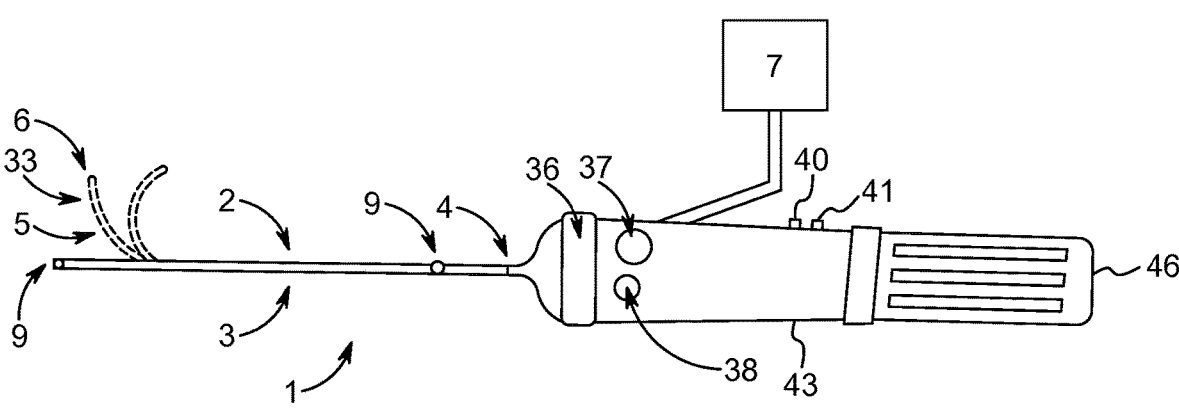
FIG. 13 shows a further embodiment of the presently disclosed negative pressure-based gripping system having an operation unit for operating a tool inside the catheter.

After being placed adjacent to the target, the negative pressure may grip and retain the target as explained. In one embodiment, the invention may thereby be seen as a system comprising a flexible catheter, which may be introduced, for example, in a femoral artery, femoral vein or other access route to the vasculature, wherein the tip is remotely controlled, and wherein the system after a gripping procedure is configured to retain the target in a fixed position in relation to the tubular body. The inventors have realized that in order to operate on a moving target, such as heart, through the catheter the target needs to be locked in relation to the catheter but not necessarily in relation to, for example, surrounding tissue. Conventional fixation tools for operating on moving targets typically are rigid and lock the target physically in relation to a fixed structure so that it cannot move. The present invention allows a more flexible approach in this sense. The system may be configured to retain a heart or a region of the heart in a fixed position as long as necessary, for example, over a number of cardiac cycles or until a given operation has been carried out. The system may comprise an inner tubular member in the tubular body of the catheter. Preferably, the inner tubular member can be inserted through the proximal end of the catheter. This may typically be done when the catheter has been correctly positioned. The inner tubular member may, for example, provide a suture or any additional tool to be used in the distal end of the catheter. The system may accordingly further comprise an operation unit configured for operating a tool or function inside the catheter. An example of such an operation unit is shown in FIG. 13.

To the extent that the present disclosure relates to 'vacuum', the term may generally be referred to a pressure much less than atmospheric pressure. In relation to the present invention, 'vacuum' and 'negative pressure' are construed broadly as an at least partial vacuum (imperfect vacuum) with the intention that a pressure in the catheter is lower than outside the catheter, in particular outside the distal opening.

Distal opening may be seen as at least one opening close to the distal end of the catheter. In one embodiment the distal opening is an open end of a tube, for example, a substantially circular open end of a tube. In another embodiment the distal opening is an opening in the side wall of the distal end section.

In one embodiment, the catheter device has an outer diameter of less than 15 mm, preferably less than 10 mm, more preferably less than 7 mm, even more preferably less than 4 mm. The catheter has a proximal end, which may be an open end of the catheter, which is typically connected to a negative pressure generator. The tubular body may be a flexible tube and may constitute a proximal section of the flexible catheter. The tubular body is then connected to, or seamlessly transformed into, the distal end section. The distal end may thereby a remotely operable and flexible part, whereas the tubular body can be a tube which, once it has been introduced, to some extend can be held in place by the vein, artery or anatomical feature, such as a septal wall, through which is was introduced.

Gripping Method, Pressure Sensor

As stated the present disclosure further relates to a method for gripping and retaining a target, preferably a moving target, such as a heart of a human or animal, in a fixed position in relation to a device. In such a process any embodiment of the presently disclosed catheter and negative pressure-based gripping system negative system may be used.

For the purpose of carrying out the described method the catheter of the system may comprise at least one pressure sensor for measuring a pressure in the catheter. The at least one pressure sensor may be located in the distal end section. It could in principle alternatively be placed anywhere in connection with the tubular body such that the system measures a pressure indicative of whether the system has gripped the target after an attempt. A plurality of pressure sensors may also be located at or integrated into various locations on the catheter in order to achieve various desired pressure readings at different points on the catheter and in the patient's circulatory system. There may, for example, be a first sensor in the tubular body and a second sensor at the distal end of the catheter. Said sensors may be used to measure pressure at various locations; pressure differentials within the catheter system, for example, to detect obstructions; and pressure differentials between the system and the fluid pressure outside the catheter, for example, relative to the patient. Typically, if the attempt to grip succeeds, a low pressure will be maintained, whereas if the gripping procedure failed, the system will keep aspirating and the pressure will not go as low as in the case of success. Such a scenario could deplete the patient of blood. Therefore, in one embodiment of the presently disclosed system, the control unit is further configured to control the operation such that the negative pressure is disconnected or disabled if the measured pressure in the flexible catheter does not remain below a predetermined pressure threshold for a predetermined period of time.

Blood Loss Prevention

A device operating by vacuum/negative pressure inside a body, for example, close to a beating heart, may face the risk of aspirating an undesired volume blood from the patient. The presently disclosed system and method may prevent blood loss by controlling the aspiration process. In addition to the control of the pressure, the system may further comprise a flush container for carrying a fluid suitable for being transferred into the human or animal, said container connected to the tubular body of the flexible catheter. After one or several successful or failed attempt(s) to grip the target the tubular body may be partly or completely filled with blood. The flush container may thereby be controlled to push and/or flush blood back into the patient in order to reduce the loss of blood. In one embodiment the control unit of the system is further configured to control the flush container such that blood aspirated during a gripping procedure is flushed back into the human or animal after a successful or unsuccessful gripping procedure. In a preferred embodiment the system further comprises an electric motor or pump arranged to push a liquid forward, in this case into the tubular body and further back into the patient, in a controlled manner. Alternatively, the liquid can be controlled by a fluid pressure or gas pressure. The flow of fluid from the flush container may thereby be achieved by electrical motor or pump controlled by the control unit.

In an alternative embodiment, a piston is used as negative pressure generator. Such a piston may be arranged such that a retraction of the piston creates a negative pressure in the tubular body. The piston may further arranged such that a further movement of the piston forward from a retracted position pushes aspirated blood during a gripping procedure back to the human or animal. The piston may manually or automatically operated.

For the purpose of flushing/pushing aspirated blood back into the patient after a griping process, the system may further comprise a sensor or other functions for measuring the amount of blood that has been aspirated during a gripping process.

Any flushing liquid suitable for this purpose may be used. This may include combinations of fluids as well as delivery of drugs, pharmaceutical and therapeutic agents, for example, anti-coagulation or rhythm management drugs may be included. Typically, saline and/or glucose could be used. The flush container may contain any such liquid.

Remotely Operable and Flexible Distal End Section

In order to locate the distal end of the catheter close to the target without direct access the target, a flexible distal end section may be used. Such a flexible distal end section may vary from a very small segment, for example, 10 mm, to a longer segment, for example, 50 mm. Preferably the remotely operable and flexible distal end section is steerable by means of mechanical force being generated in the handle of the device with our without computer-assisted control. The remotely operable and flexible distal end section may comprise tendons or other mechanical elements such as cams, rotating wall sections, active materials, pneumatics or hydraulics for controlling movement and articulation of the distal end, preferably wherein the tendons extend along from the tubular body along the distal end section. The distal end section may also comprise a robotic section, such as a robotic tubular arm, preferably having multiple segments and/or multiple joints, controlled by the control unit. Preferably, the distal end section, in particular the distal opening, is controlled while keeping track of its exact position by means of an imaging system, for example, based on ultrasound, x-ray based imaging or other imaging techniques. Such imaging systems can be external or internal to the patient or integrated into the catheter device, for example, ultrasound imaging integrated into the catheter. In order to further improve the orientation of the device, the catheter may further comprise a sensor in the distal for orienting the tip in relation to another device or component. The sensor may be, for example, an impedance sensor, a flux field coil or a magnet configured to sense the presence of an adjacent current and/or magnetic field from another device or component. One example of an application that would benefit from this embodiment is the process of mitral valve annuloplasty or mitral valve plasty, wherein a ring is inserted into the coronary sinus and indirect annuloplasty performed. In such a scenario it would be possible that the presently disclosed negative pressure-based gripping system operates on the inside of the mitral valve, whereas the ring is placed outside the valve to create tension or a constricting force transmitted to the mitral valve and the mitral annulus.

It may be an advantage that the system is capable of locking the flexible distal end section when it has successfully gripped the target by means of vacuum inside the tubular body. Therefore, in one embodiment of the catheter and system, the remotely operable and flexible distal end section can be locked in a rigid configuration. Both the tendons and the robotic construction embodiments may be used in this regard to lock the flexible distal end section in the rigid configuration. The device may further comprise a switch for selecting between a rigid configuration and a configuration wherein distal end section is flexible.

Operation in Distal End Section

One advantage of the presently disclosed catheter and system is that an operation may be carried out through the catheter which may be positionally locked in relation to a moving target. It may thereby be acceptable to allow the target to continue to move, either freely or limited, during operation. In particular if further equipment is placed inside or in positional relation to the catheter and the catheter is positionally locked by vacuum in relation to the target, from the perspective of this equipment, even a moving target will be seen as a fixed target.

In one embodiment the distal end section comprises an end section chamber for further tools arranged to operate on the target. This kind of equipment may, for example, be a contact element for transferring energy, such as radiofrequency, ultrasound and laser energy or cryotherapy, to the target. The contact element is preferably arranged at the distal opening. The device may further comprise a wire in the tubular body connected to a contact element arranged at the distal opening, wherein the contact element is configured to transfer energy, such as active radiofrequency energy, to the target, preferably wherein the target is tissue, such as tissue of a heart. The contact element should not block the tubular body, through which the vacuum needs to be generated. In one embodiment the contact element is arranged in the center of the distal opening, and/or wherein the contact element does cover the entire distal opening. This embodiment may further comprise an energy generator configure to generate energy to the contact element through the wire. Use of this technology is further explained under methods and applications below.

In a further embodiment, the catheter wall, itself, is the element for transferring energy as described above. In this case, as in the aforementioned embodiment, the energy transfer element may include segments of differing polarity and phase so as to enable unipolar, multi-polar and multi-phase transfer of energy.

One of the useful mechanisms that may be included in the distal end of the catheter is a mechanism for holding on to tissue drawn in through the distal opening. Such a gripping and/or cutting mechanism may comprise a first gripping/cutting part and a second gripping/cutting part arranged on opposite sides of the distal opening. If the parts are moved towards each other when tissue has been aspirated into the catheter, they can lock the tissue mechanically. This mechanism can be handled by means of wires or by robotic control. The mechanism can enable for operation/treatment of or through the aspirated and locked tissue. For example, the device and system may further comprise a mechanism for remotely anchoring surgical sutures, tethers, fasteners, clips, meshes, textiles, implants, or drug delivery devices in tissue aspirated through the tubular body. Such an application may benefit from a further mechanical fixation in addition to the vacuum based retention. It may useful to have an inner tubular member in the tubular body of the catheter. The inner tubular member may, for example, provide a suture, or may provide any other of the mechanisms described in the present disclosure. Optionally, if the suture is to be fastened to two targets and the length adjusted accordingly, the suture may enter through the inner tubular member and return to a space defined between the inner tubular member and the catheter.

As an example, the same kind of mechanism can be used to staple tissue, such as a segment of a valve of a heart. In one embodiment the device further comprises a stapling or fastening mechanism at the distal opening. The stapling mechanism may comprise a first stapling part and a second stapling part arranged on opposite sides of the distal opening, wherein tissue aspirated through the distal opening is stapled by moving the first stapling part and the second stapling part towards each other and driving a metal, polymer or bioabsorbable staple, clip, fastener, formed wire or a thread through the tissue. The two parts can also, if they are made sharp, be used for cutting aspirated tissue. The fastening mechanism may comprise a helical anchor. A suture may be attached to the fastening mechanism. As an example, a suture may be attached to a helical anchor. If the anchor is fastened to a target, for example, tissue, the suture will also be attached and can then be cut. A suture may comprise a first side arranged in the inner tubular member, and a second side returning through a space defined by the inner tubular member and the catheter.

The catheter and the negative pressure-based gripping system may further comprise a puncturing mechanism inside the tubular device, wherein the puncturing mechanism is arranged to puncture tissue, aspirated by generated negative pressure, preferably wherein the puncturing mechanism is remotely operable. The puncturing mechanism preferable is mounted in a fixed position in relation to the flexible distal end section. The puncturing mechanism typically comprises a needle. The needle may be controlled by a wire, tube or mechanical element capable of performing axial displacement through the flexible catheter. Alternatively, the needle is controlled by fluid in a channel through the tubular body. The control unit may thereby be configured to control the pressure in the channel such that an increase pressure moves the needle forward and a decreased pressure moves the needle backwards.

A variant of the needle is a remotely operated hollow needle or cannula through which a substance can be injected into the target in the locked position. The hollow needle or cannula may be connected to a chamber comprising the substance to be injected. The substance in the chamber can be injected into the target by a pump or a plunger pushing the content of the chamber forwards. The plunger may be connected similarly to a needle, i.e. by means of a wire or by a channel comprising fluid and a control unit for controlling the pressure in the channel to move the plunger. Such a construction may have a two-step actuation mechanism, wherein forwards movement of the hollow needle and plunger are controlled in two steps, where the hollow needle is moved forward in a first step and the plunger is moved forward in a second step, thereby injecting the substance. Such a process in illustrated in FIGS. 9A-D.

Method for Gripping and Retaining a Target—Use and Applications of the System The present disclosure further relates to a method for gripping and retaining a target, preferably a moving target, such as a heart of a human or animal, in a fixed position in relation to at least a part of a device. Preferably the method is carried out using an embodiment of the presently disclosed catheter and negative pressure-based gripping system for gripping and retaining a target. Once the target has been gripped the method may comprise additional steps for performing different operations on the target.

The method may comprise the steps of steps of:

providing a device having a catheter having a tubular body; a proximal end; and a remotely operable and flexible end section with a distal opening;

positioning the distal opening adjacent to the target by steering the distal end remotely; and generating a negative pressure in the tubular body.

The provided device may be any embodiment of the presently disclosed device or system having a catheter having a tubular body; a proximal end; and a remotely operable and flexible end section with a distal opening.

In order to ensure that the patient is not depleted of blood the method may further comprise the following steps of during the gripping procedure:

measuring the pressure in the tubular body for a predefined period of time;

if the measured pressure remains below a predefined pressure threshold for longer than a predefined period of time, maintaining the negative pressure in the tubular body to retain the target, otherwise disabling the negative pressure.

The method may further comprise the step of flushing the tubular body with a fluid suitable for being transferred into the human or animal towards the distal end of the device, thereby flushing blood back into the human or animal upon a successful or unsuccessful gripping and retaining procedure. Alternatively, or in combination, the method may further comprise the step of pushing or reinfusing aspirated blood back into the human or animal upon a successful or unsuccessful gripping and retaining procedure. As an example, a flush container for carrying a fluid suitable for being transferred into the human or animal, said container connected to the tubular body of the flexible catheter, can be used for this purpose The method may then comprise the step of controlling an electric motor to push the fluid into the tubular body and into the patient after a successful or unsuccessful gripping procedure. Such a procedure may comprise measurement of the amount of aspirated blood in order to know how much blood that needs to be flushed back into the patient. In the case of the method comprising further subsequent steps of, for example, treatment and/or surgery, it should be understood that the flushing process may be applied after the additional steps, i.e. the sequence may thereby be, for example: successful gripping—treatment— flushing. Another possible sequence would be: unsuccessful gripping—successful gripping—treatment—flushing.

The method for gripping and retaining a target may further comprise the step of introducing the device by a vein or an artery of the human or animal before positioning the distal opening. This is possible using a flexible catheter, for example, a flexible catheter that is arranged to be introduced transfemorally to access the heart. By having a relatively small and thin catheter and remotely operable distal section it is possible to operate less invasively from the outside, for example, by inserting the catheter through the femoral vein.

As stated the method may further comprise the step of providing therapy, treatment or surgery to the target. Examples of such processes will now be given in relation to the presently disclosed negative pressure-based gripping system and method.

In one embodiment the method further comprises the step of applying energy to the mitral annulus and tissues of a heart through a contact element arranged at the distal opening. The method can thereby be said to be a method for mitral annuloplasty. A mitral annuloplasty can be performed in two different ways. By applying energy to the mitral annulus (Radiofrequency, heat, cold, radiation, ultrasound, microwaves and other forms), the annulus will shrink and thereby performing a mitral annulus reduction plasty. To apply energy, the energy source must be close to the annulus for a longer period of time—this can be achieved by applying the presently disclosed method. A mitral annuloplasty can also be performed by placing serial screws in the annulus as anchors and then pulling them together with a wire or, alternatively, placing suture or wire loops through the tissue to draw the tissue together. The present method can facilitate a catheter based stiffening and shrinking of the annulus and cardiac tissues. By sequentially capturing segments of the mitral annulus and cardiac tissues, energy can be delivered to the entire length of the annulus. The procedure may comprise the steps of:

1. Introducing the device in the femoral or jugular vein
2. Using a guidewire to enter the right atrium
3. Puncturing the atrial septum, using an internal needle, for example
4. Crossing the septum with distal end of the device
5. By ultrasound guidance locating the device so that the opening at the top is located above the correct segment of the annulus
6. Activating negative pressure so the device is fixed at the right spot 7. Activing radiofrequency or other energy source
8. Disconnecting the negative pressure
9. Iterating, for example, 10-15 times, until the length of the annulus has been treated
10. Extracting the device.

Steps 5-6 may correspond to the presently disclosed method for gripping and retaining a moving target.

In one embodiment the method further comprises the step of stapling or fastening a valve part of the mitral valve. This method can be used in relation to, for example, mitral leaflet prolapse. The method can thereby be said to be a method for treatment of mitral annuloplasty The present method can facilitate a catheter-based resection made on beating heart. By capturing the part of the mitral valve that has prolapse, it can be reduced by means of stapling technology. The procedure may comprise the steps of:

1. Introducing the device in the femoral or jugular vein
2. Using a guidewire to enter the right atrium
3. Puncturing the atrial septum, using an internal needle, for example
4. Crossing the septum with the device
5. By ultrasound locating the device so that the opening in side is located above the segment that has prolapse (usually P2 segment)
6. Activating negative pressure so that part of the valve is aspirated in to the opening
7. Using the staple or fastening function of the instrument to reduce the segment of the valve
8. Extracting the device.

Steps 5-6 may correspond to the presently disclosed method for gripping and retaining a moving target.

In particular the steps of:

1. Introducing the device in the femoral vein
2. Locating the distal end device so that the opening in side is located adjacent to a particular area to be treated may be important in combination with the step of further holding/locking tissue aspirated through the distal opening mechanically by means of, for example, a first gripping part and a second gripping part arranged on opposite sides of the distal opening which are moved towards each other when tissue has been aspirated into the catheter.

From this position further steps can be performed. In one embodiment the method further comprises the step of anchoring or attaching a medical component to the target. This can be used, for example, in relation to a pacemaker lead insertion or a chordae replacement.

Chordae rupture is a common disease of the mitral valve. A chordae is structure that tethers the mitral valve and stops it from flaring up and becoming incompetent. If a chordae ruptures, the mitral valve will not close properly, and becomes incompetent.

The presently disclosed method can be used for chordae replacement. In this embodiment the method may comprise the steps of:

1. Introducing the device in the femoral or jugular vein
2. Using a guidewire to enter the right atrium
3. Puncturing the atrial septum
4. Crossing the septum with the device
5. By ultrasound locating the device so that the end is located on a papillary muscle
6. Activating negative pressure so the papillary muscle is captured
7. Fixating a suture in the papillary muscle using a screw, anchor, such as a helical anchor, or other fixation technique
8. Deactivating the negative pressure 9. Moving the device to the leaflet of the mitral valve that has a ruptured chordae 10. Activating negative pressure so the leaflet of the mitral valve is captured 11. Fixating a suture in the mitral leaflet using a screw, anchor, or other fastener technique 12. Deactivating the negative pressure 13. Adjusting the length of the two sutures so that the valve becomes competent 14. Locking the length of the sutures 15. Cutting sutures 16. Extracting the device As a person skilled in the art would understand, the steps do not necessarily have to be performed in the above order.

Therefore, the present disclosure further relates to a method for performing mitral valve chordal repair of a heart, comprising the steps of:

providing a device having a catheter having a tubular body; a proximal end; and a remotely operable and flexible end section with a distal opening;

introducing the device in the femoral or jugular vein;

positioning the distal opening adjacent to the target by steering the distal end remotely;

using a guidewire to enter a right atrium of the heart;

puncturing an atrial septum and crossing the atrial septum of the heart;

locating, such as by ultrasound, the device so that the end is located on a papillary muscle generating a negative pressure in the tubular body, thereby locking the distal opening to a papillary muscle of the heart;

fixating a suture, such as by anchoring a helical anchor, in the papillary muscle;

releasing the negative pressure and moving the device to the leaflet of the mitral valve that has a ruptured chordae;

generating a negative pressure in the tubular body, thereby locking the distal opening to the leaflet of the mitral valve;

fixating a suture, such as by anchoring a helical anchor, in the mitral leaflet;

adjusting the length of the two sutures so that the valve becomes competent.

Accordingly, the disclosure further relates to an apparatus for performing mitral valve chordal repair of a heart, the apparatus comprising any embodiment of the presently disclosed negative pressure-based gripping system.

In the process of performing mitral valve chordal repair of a heart, the step of adjusting the tether for mitral chordae repair may be particularly challenging. The present disclosure further relates to an embodiment of the negative pressure-based gripping system further comprising a mechanism for performing the adjustment of the suture or tether, which is exemplified in FIG. 14. The device has in inner tubular member in the form of a snare through which the tether extends and an outer lock pusher sheath that can be pushed along the snare to fasten a lock element against, for example, a helical anchor to lock the tether/suture. A snare inside the catheter may be designed, preferably as thin as possible, such that the valve function and leaflet apposition could be observed on a beating heart while minimally disturbing the leaflet during tensioning and locking of the tether. If only the snare extends through the valve during operation and the snare is adequately thin, good visible leaflet apposition against the thin snare is possible. This may better preserve the advantage of performing the procedure on a beating heart and enhance ability to observe the valve dynamic achieved by tether length adjustment. A process of performing mitral valve chordal repair of a heart, using this device, may comprise the following steps:

placing a first helical anchor in a leaflet, thereby creating a first point of tether attachment placing a second helical anchor in the papillary muscle to create a second point of tether attachment slidably adjusting the length of the tether through the snare by applying tension to the remaining tether extension so that it glides over the second helical anchor until desired leaflet function and apposition is achieved positioning a tether lock at the end of the snare and over the second helical anchor when desired tether length is achieved, locking the tether to the second helical anchor by stabilizing the inner portion of the lock by holding the snare in tension, while slidably applying a compressive force on the outer portion of the lock with a lock pusher sheath The lock may be implemented, for example, by having inner and outer lock components, which can be locked by a ratcheting or snap-fit feature or the like.

The method may further comprise the step of puncturing the target by using a puncturing mechanism inside the tubular device at the distal opening. As explain the puncturing mechanism may involve the use of a needle arranged inside the distal end section through the distal opening. The puncturing may be performed either as a treatment step after having gripped the target or as a means of entering a specific location within a heart, for example, by puncturing the atrial septum and subsequently crossing the septum with the device.

The puncturing may also be made by a hollow needle, wherein the puncturing is followed by the step of injecting a substance into the target through the hollow needle.

DETAILED DESCRIPTION OF DRAWINGS

The invention will in the following be described in greater detail with reference to the accompanying drawings. The drawings are exemplary and are intended to illustrate some of the features of the presently disclosed negative-pressure based system and method, and are not to be construed as limiting to the presently disclosed invention.

Figure 1:
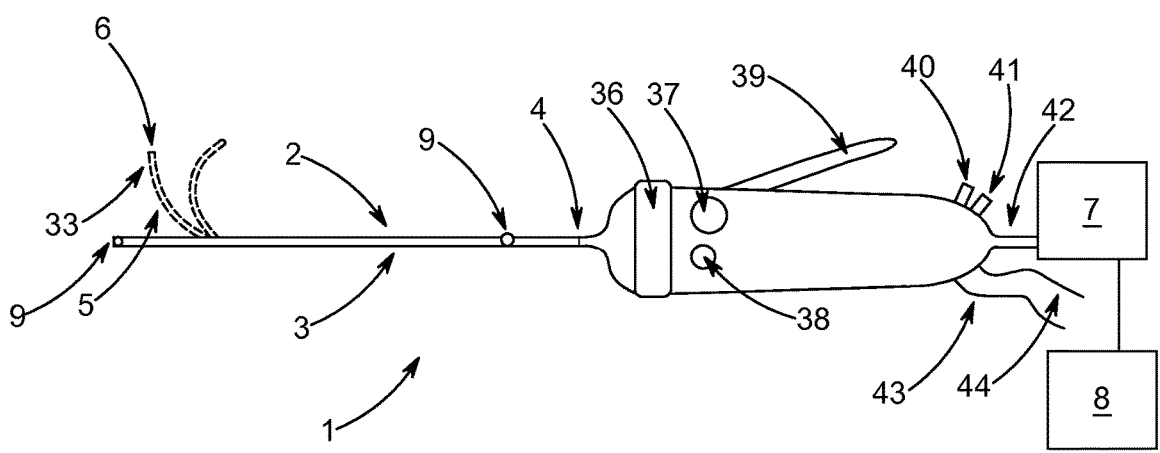
FIG. 1 shows an embodiment of the presently disclosed negative pressure-based gripping system for gripping and retaining a target.

FIG. 1 shows an embodiment of the presently disclosed negative pressure-based gripping system (1) for gripping and retaining a target. The embodiment shows a handheld device with an external negative pressure generator (7) connected to the catheter (2). The system (1) has a catheter (2) having a tubular body (3) having a proximal end (4) connected to a negative pressure generator (7). The catheter has a flexible distal end section (5) with a distal opening (6) at the distal end (33). The distal end section (5) is shown in three different positions. A control unit (8) controls the negative pressure generator (7) and the positioning of the distal end section (5), in particular the distal end (33). There is a first pressure sensor (9) in the tubular body (3) and a second sensor (9) at the distal end of the catheter (2). In this handheld embodiment the device comprises a positioning control element (36) for positioning the distal end (33) in the form of a wheel (36) for controlling the flexing the distal end section (5). The embodiment further comprises a feedback light (37) for indicating, based on values from the pressure sensor (9) whether the system has gripped the target after an attempt. There is also a pressure control button (38) for directly activating/deactivating the negative pressure. A lever (39) controls additional functionality at the distal end

(33) of the device, which may be, for example, actuation of stapling/RF treatment or deployment of stich. The device has further ports for communicating with external sources and devices, including a port (40) for fluid or RF connection and ports for connecting an external negative pressure generator and a pressure outlet (41, 42). Depending on the embodiment the device may further comprise an electrical cable (43) and a guide wire port (44) for receiving a guidewire that can be used through the catheter (2). As explained in the present disclosure, different partitioning of the functions and components between a handheld device and a central is possible and depend on the context and use of the device/system. For example, the guidewire port (44) is optional and the gripping feedback may be presented on a screen rather than as a feedback light on the device.

Figure 2:
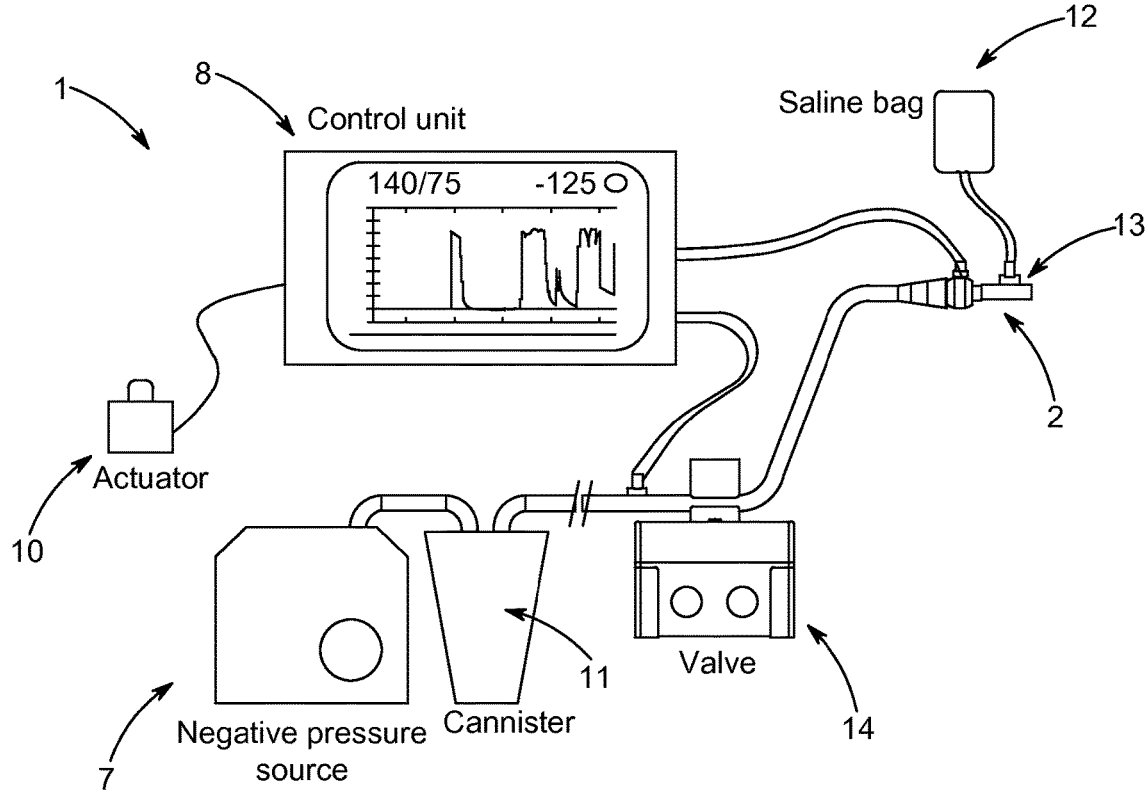
FIG. 2 shows another embodiment of the presently disclosed negative pressure-based gripping system for gripping and retaining a target.

FIG. 2 shows another embodiment of the presently disclosed negative pressure-based gripping system (1) for gripping and retaining a target. In this embodiment the system comprises a flush container (12) which has a connection (13) to the catheter (2). The embodiment comprises a control unit (8) which has a manual actuator (10) for interrupting the generation of negative pressure based one a monitored pressure. The embodiment further comprises a canister (11) which can be used for collecting blood and tissue that has been cut by the device. The system further comprises a valve (14).

Figure 3A:
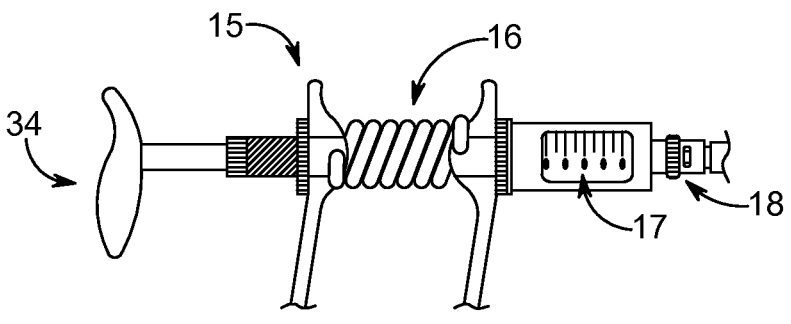
FIG. 3 shows an embodiment of a piston for creating a negative pressure in the tubular body.
Figure 3B:
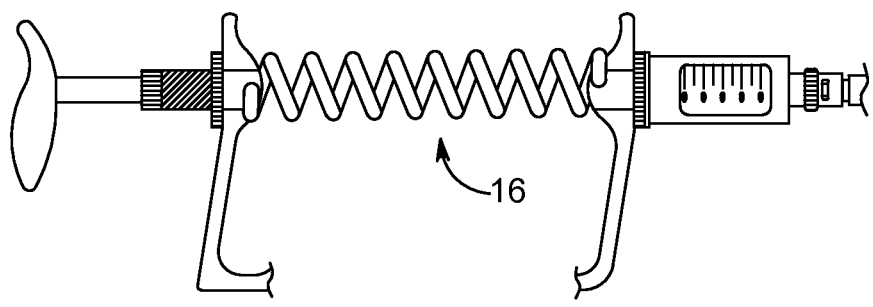

FIG. 3 shows an embodiment of a piston mechanism (15) for creating a negative pressure in the tubular body. The piston mechanism (15) has a connection (18) and a chamber in which a user can see on a scale (17) how much blood that has been aspirated. The piston mechanism (15) has spring (16) and a manual actuator (34) for operating the spring (16). In FIG. 3A the spring is in a compressed position. In FIG. 3B the spring has been retracted to create a negative pressure. If the spring returns to the compressed position, aspirated blood can be pushed back into the patient.

Figure 4A:
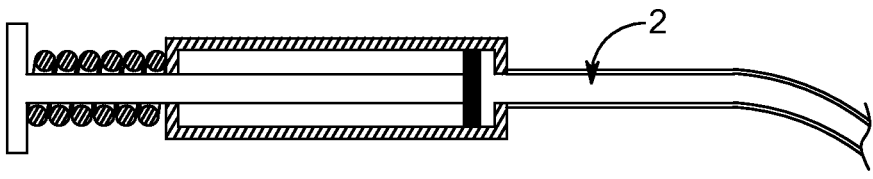
FIG. 4 shows another embodiment of a piston for creating a negative pressure in the tubular body.
Figure 4B:
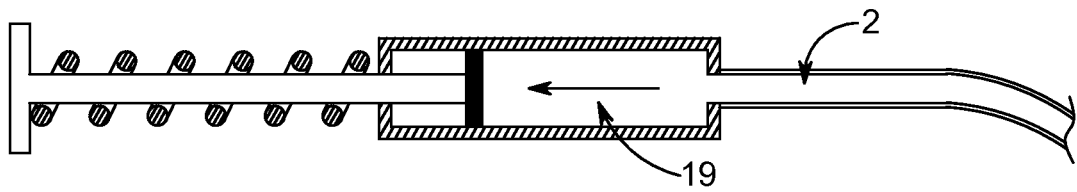
Figure 5A:
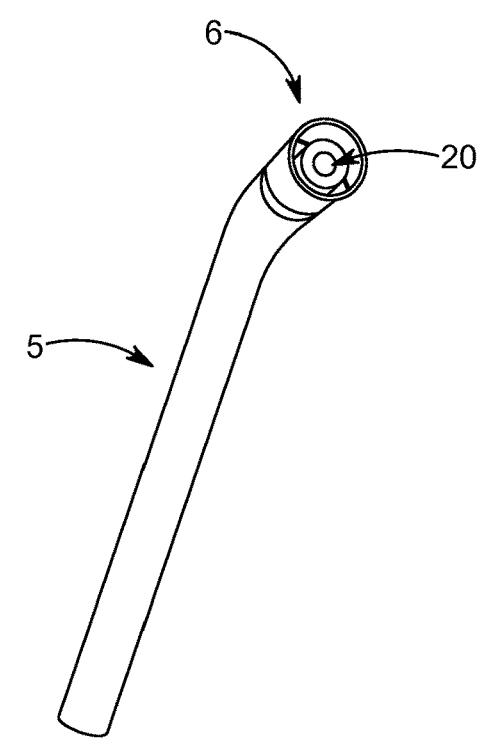
FIG. 5 shows an embodiment of the catheter wherein the distal section comprises an element for applying energy (such as radiofrequency) to the target through the distal opening.
Figure 5B:
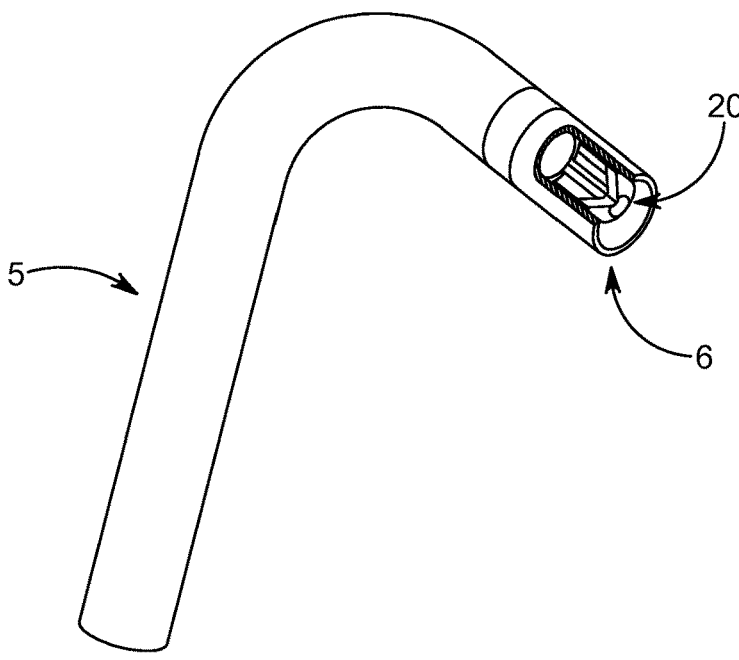
Figure 5C:
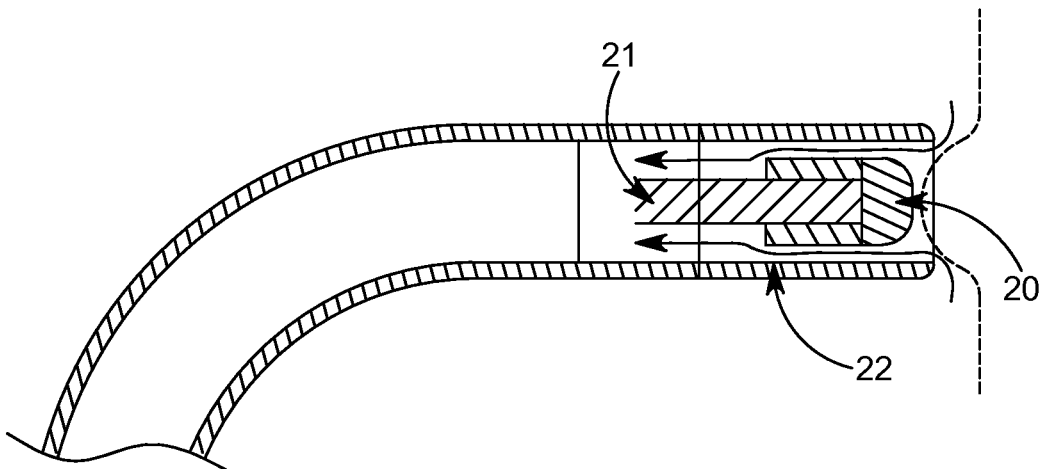
Figure 5D:
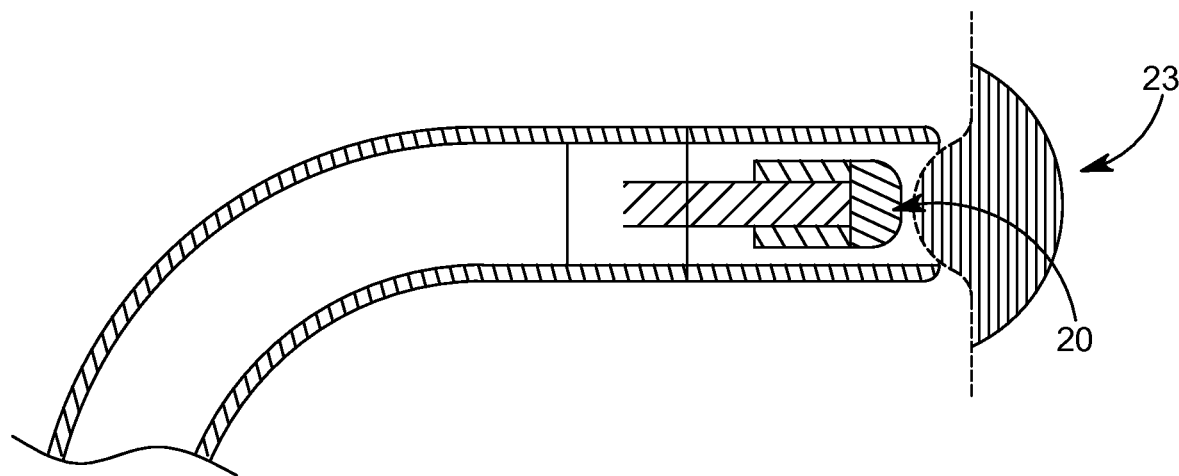
Figure 6A:
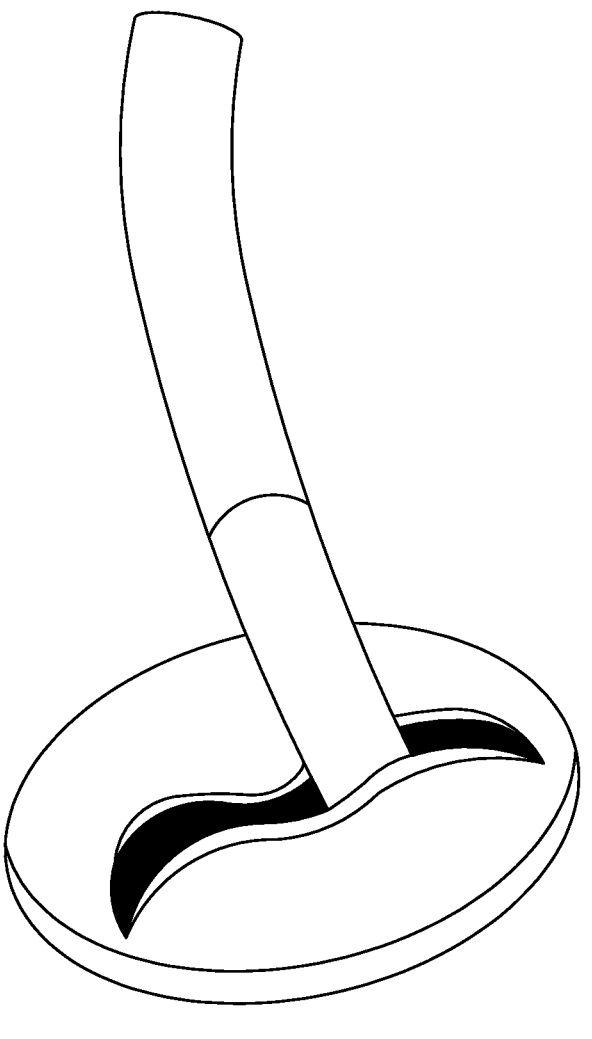
FIG. 6 shows an embodiment of the catheter having a stapling function wherein a staple, clip or fastener fixates the tissue drawn in by the negative pressure, for example, to remodel the valve leaflet or target tissue.
Figure 6A:
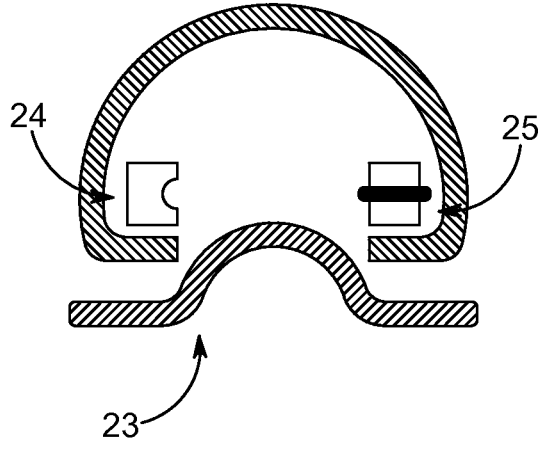
Figure 6B:
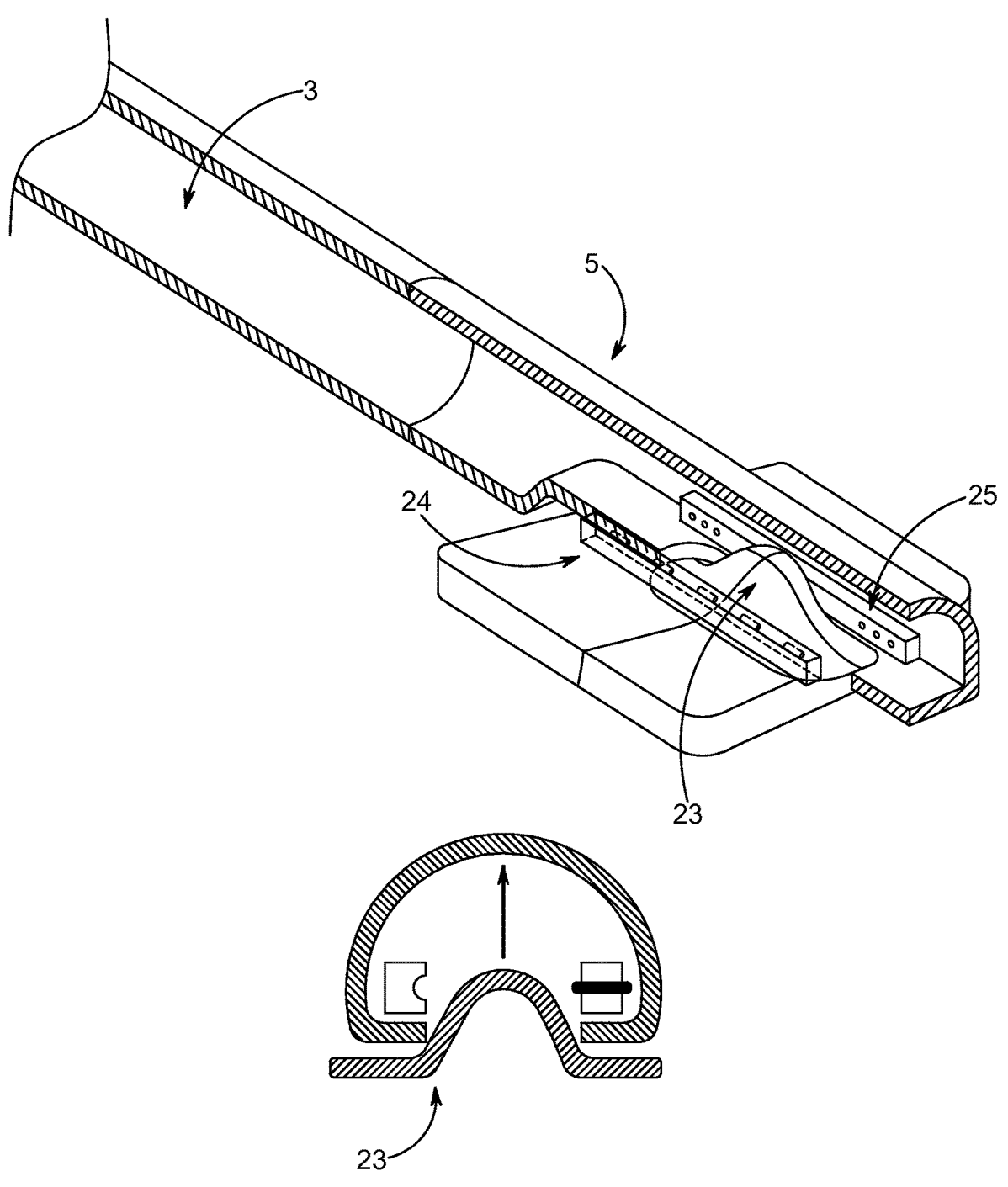
Figure 6C:
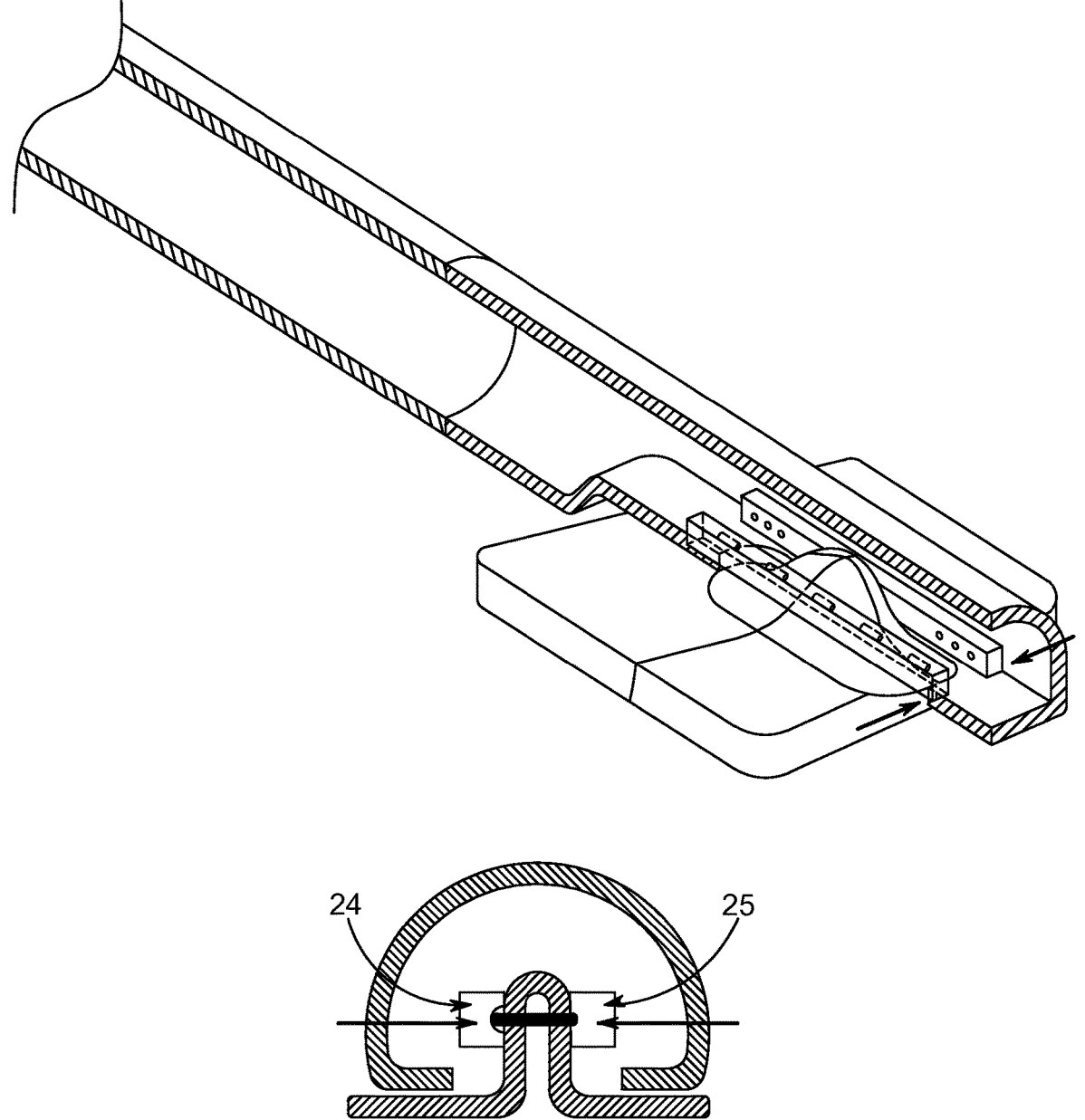
Figure 7A:
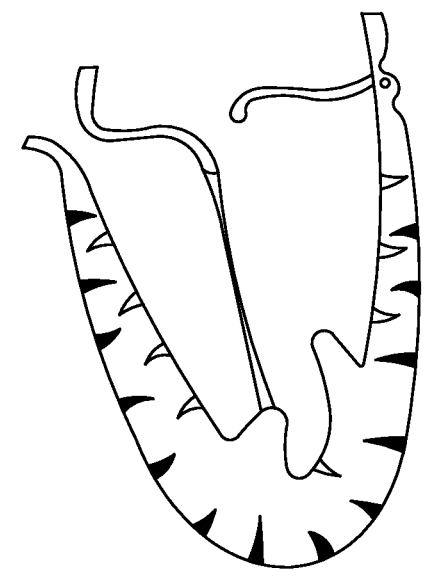
FIG. 7 shows a process of screwing or anchoring into a target using the presently disclosed negative pressure-based gripping device.
Figure 7B:
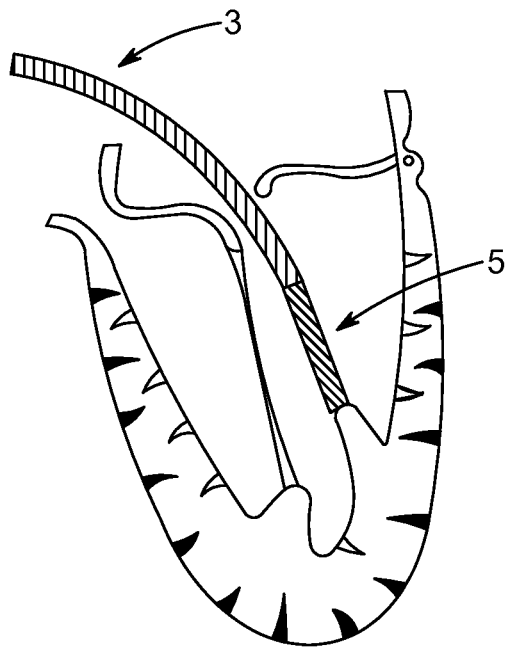
Figure 7C:
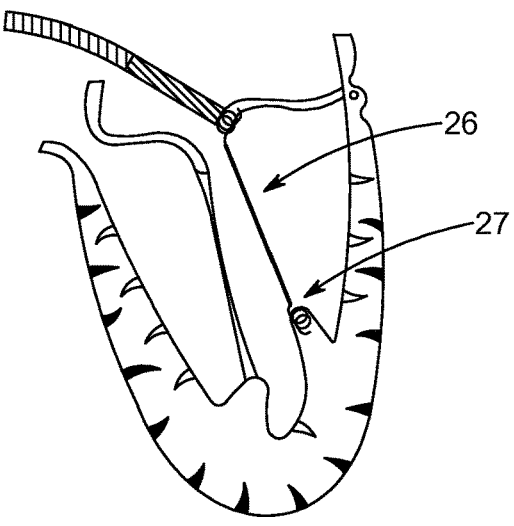
Figure 7D:
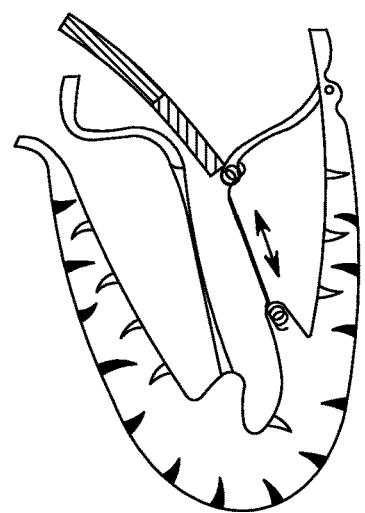
Figure 7E:
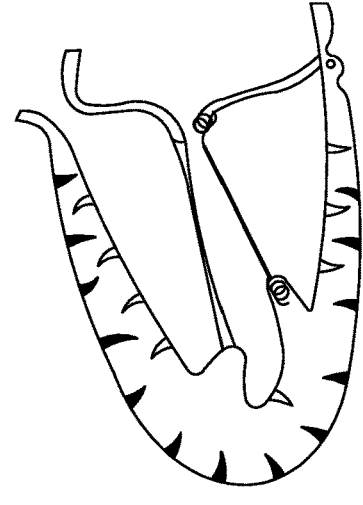

FIG. 4 shows another embodiment of a piston mechanism (15) for creating a negative pressure in the tubular body. A chamber (19) is in fluid connection with the catheter (2). The function is otherwise similar to the function of FIG. 3.

FIG. 5 shows an embodiment of the catheter (2) wherein a distal section (5) comprises an element (20) for applying energy (such as radiofrequency) to the target through the distal opening (6). It can be seen in FIG. 5C that the element (20) is arranged in the middle of the distal opening (6), leaving a passage (22) open for the generation of negative pressure. The element (20) is connected through a cable (21) in the catheter. FIG. 5D illustrates how the element (20) applies energy to a target (23) retained by the negative pressure generated inside the catheter.

FIG. 6 shows an embodiment of the catheter having a stapling function. A tubular body (3) seamlessly extends into a distal end section (5) having a distal opening. There are two a first gripping/stapling mechanism (24) and a second gripping/stapling mechanism (25) for retaining and in this case stapling aspirated tissue (23). The same mechanism can be used for retaining an aspirated target mechanically for further treatment. The distal opening may be placed in the same way on a distal opening on a distal end of a tube, i.e. an open end of a tube. It would also be possible to fixate or attach to the tissue (23) using a helical screw or anchor.

FIG. 7 shows a process of screwing or anchoring into a target using the presently disclosed negative pressure-based gripping device, in this case a chordae replacement. In FIG. 7B the papillary muscle is captured and a suture (26) is fixated using a screw and/or anchor (27). In FIG. 7C the distal opening of the device is moved to the leaflet of the mitral valve that has a ruptured chordae and the suture (26) is fixated in the mitral leaflet using a screw, anchor, or other technique. In FIG. 7D the length of the two sutures is fixated. In FIG. 7E the sutures are cut. The presently disclosed device may be attached to the targets in the position of FIG. 7B and position of FIG. 7D. As can be seen from FIGS. 7C-7E, a helical attachment, in the form of, for example, a coil, can be used to fixate the suture (26).

Figure 8A:
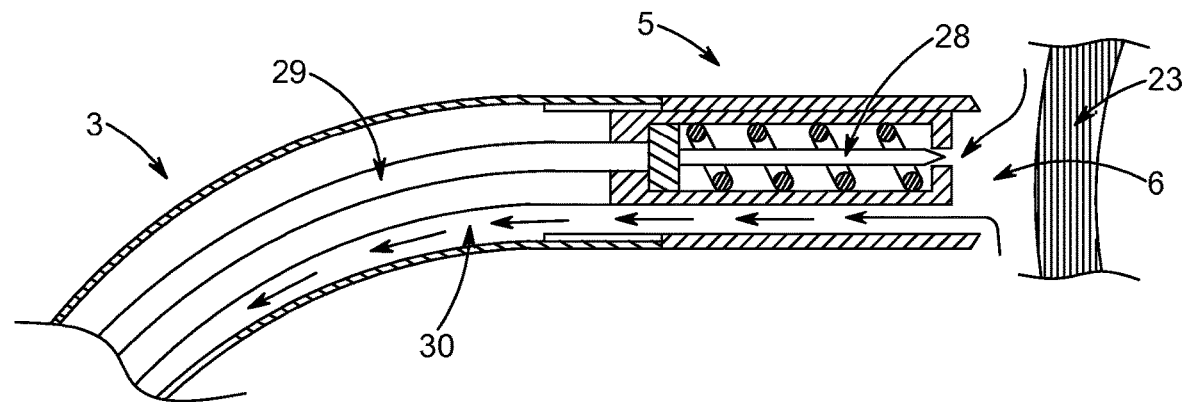
FIG. 8 shows an embodiment of the presently disclosed negative pressure-based gripping system having a pressure-controlled needle.
Figure 8B:
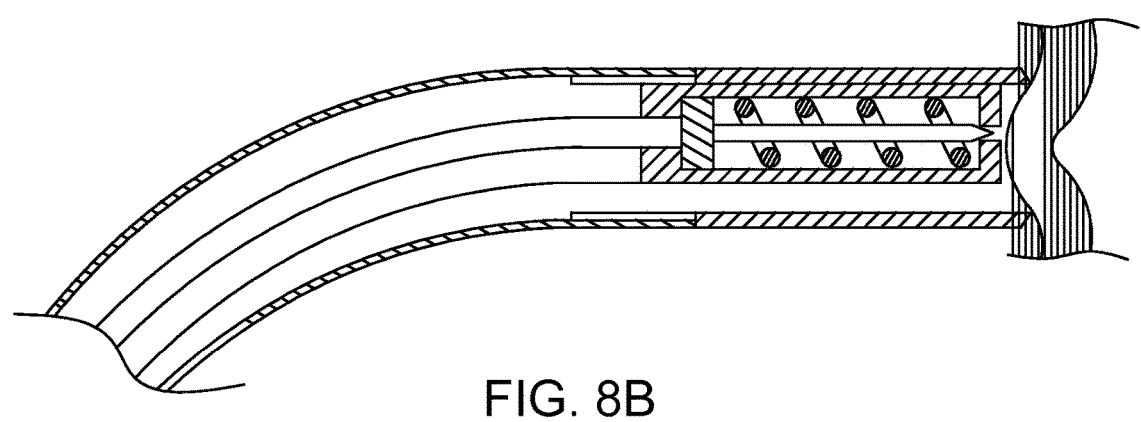
Figure 8C:
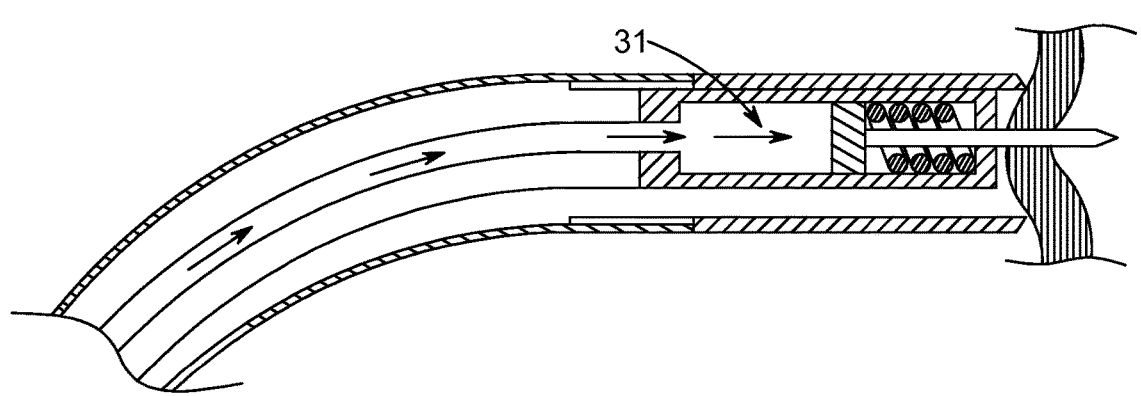
Figures 9A, 9B, 9C, 9D:
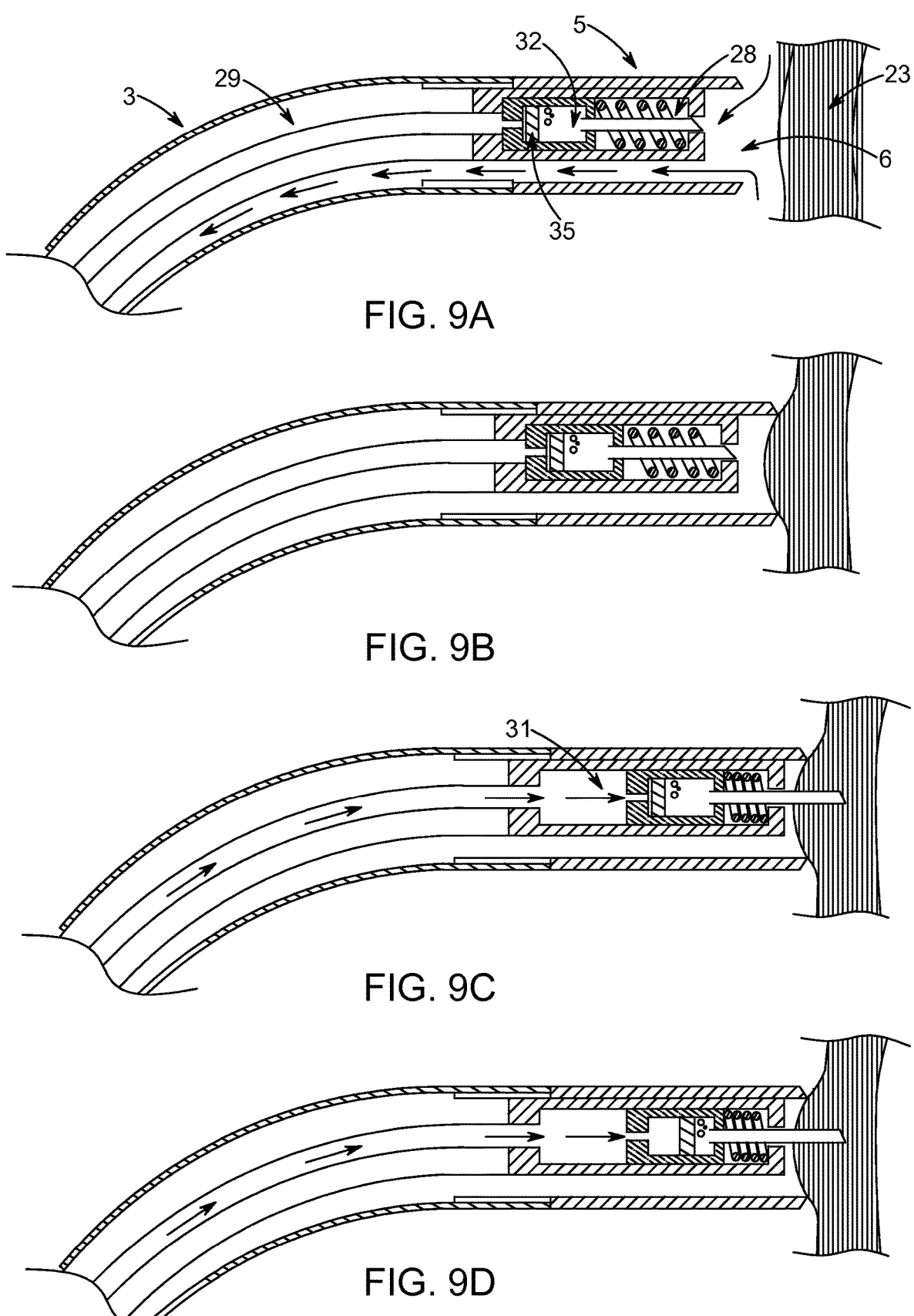
FIG. 9 shows an embodiment of the presently disclosed negative pressure-based gripping system having a pressure-controlled hollow needle and chamber comprising a substance to be injected.

FIG. 8 shows an embodiment of the presently disclosed negative pressure-based gripping system (1) having a pressure-controlled needle (28) in the distal end section (5). The catheter has a passage (30) for the negative pressure. When the negative pressure has been applied and the target (23) has been aspirated and is retained through the distal opening (6), the needle (28) can be controlled by fluid through a channel (29) and chamber (31) in fluid connection by controlling the pressure of the fluid.

FIG. 9 shows an embodiment of the presently disclosed negative pressure-based gripping system (1) having a pressure-controlled hollow needle (28) and second chamber (32) comprising a substance to be injected into the target (23). When the negative pressure has been applied and the target (23) has been aspirated and is retained through the distal opening (6), the needle (28) can be controlled by fluid through a channel (29) and chamber (31) in fluid connection by controlling the pressure of the fluid. In a first step the spring (28) is compressed by the increased pressure and punctures the target (23). In a second step the same fluid continues to push a plunger (35) forwards toward the distal opening (6) and pushes the substance of the second chamber (32) into the target.

Figure 10:
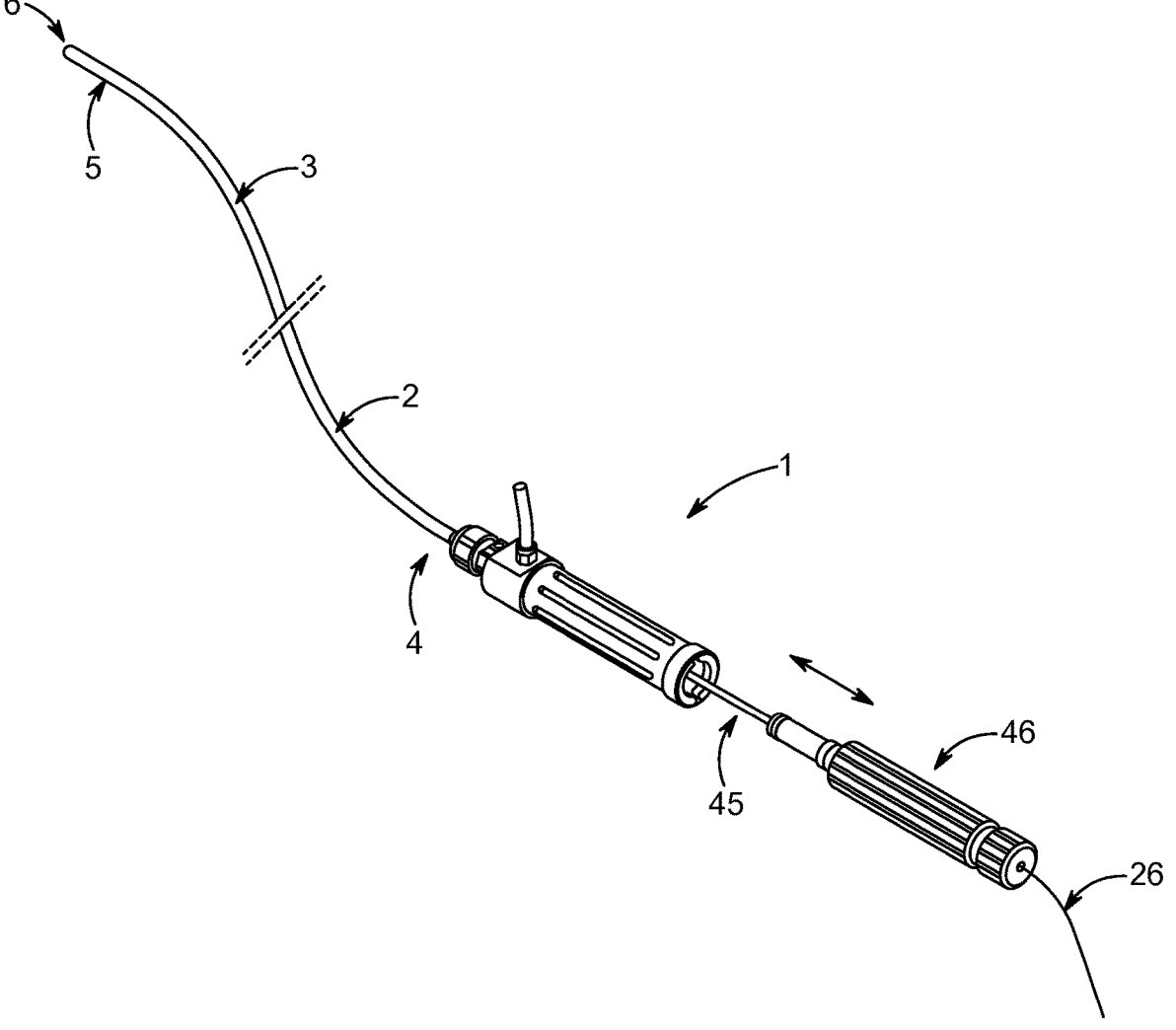
FIG. 10 shows an embodiment of the presently disclosed negative pressure-based gripping system.

FIG. 10 shows an embodiment of the presently disclosed negative pressure-based gripping system (1). The system (1) has a catheter (2) having an outer tubular body (3) having a proximal end (4) connected to a negative pressure generator (not visible). The catheter has a flexible distal end section (5) with a distal opening (6). An inner tubular member (45) can be inserted through the proximal side of the outer tubular body (3). The system further comprises an operation unit (46) for operating a tool that has been inserted in the inner tubular member (45). Such a tool could be, for example, a helical anchor and/or a puncturing tool and/or a clipping and/or a fastening tool and/or a fixation tool. In the example a suture (26) enters the inner tubular member (45) through the operation unit (46).

Figure 11A:
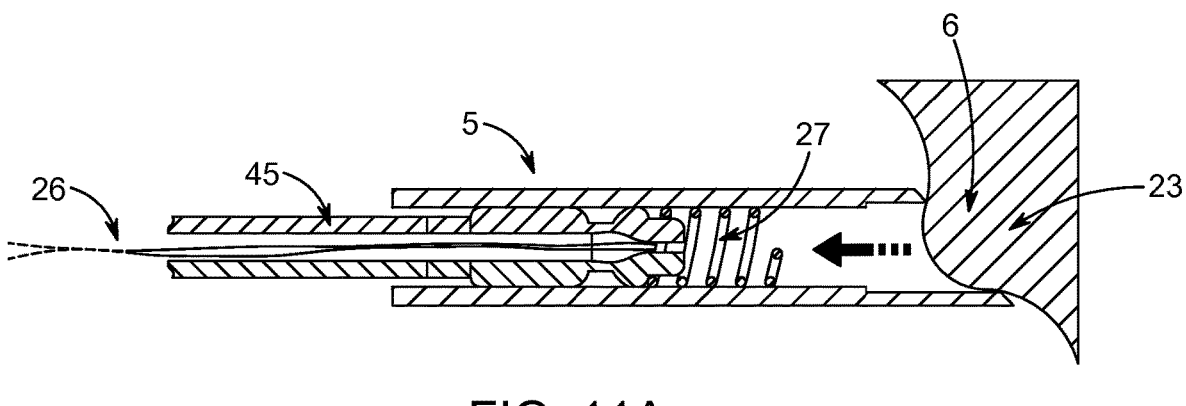
FIG. 11 shows an embodiment of the catheter comprising a mechanism for fixating or anchoring a helical anchor and optionally a suture to a target.
Figure 11B:
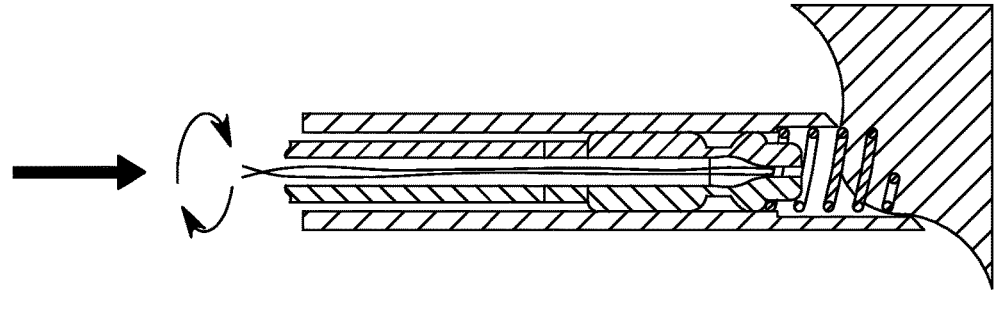
Figure 11C:
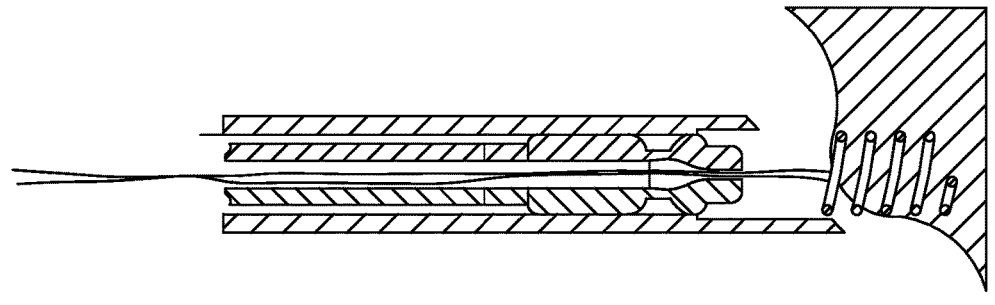
Figure 12A:
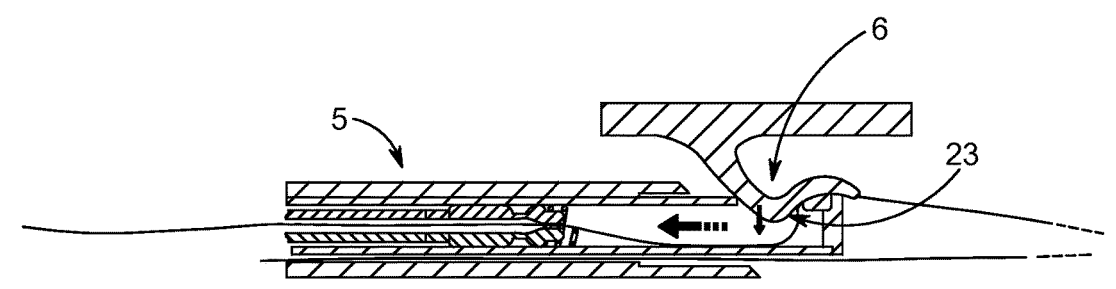
FIG. 12 shows a further embodiment of the catheter comprising a mechanism for fixating or anchoring a helical anchor and optionally a suture to a target.
Figure 12B:
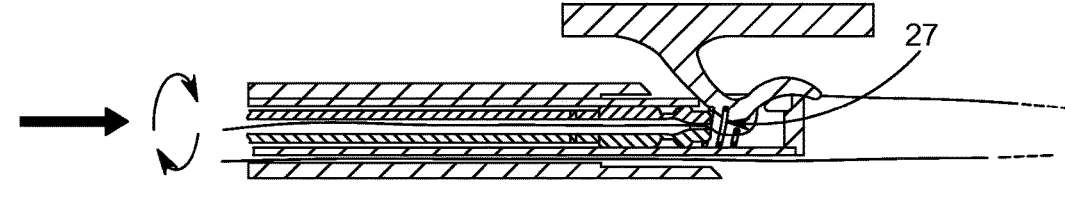
Figure 12C:
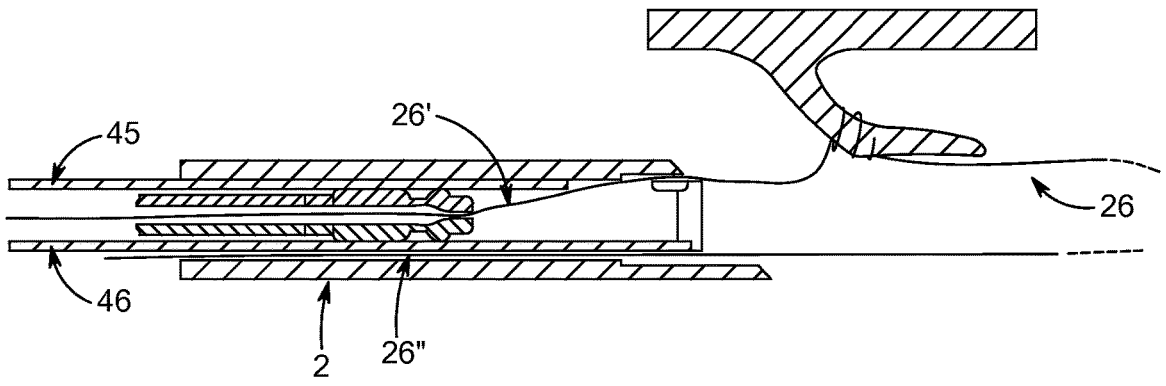
Figure 12D:
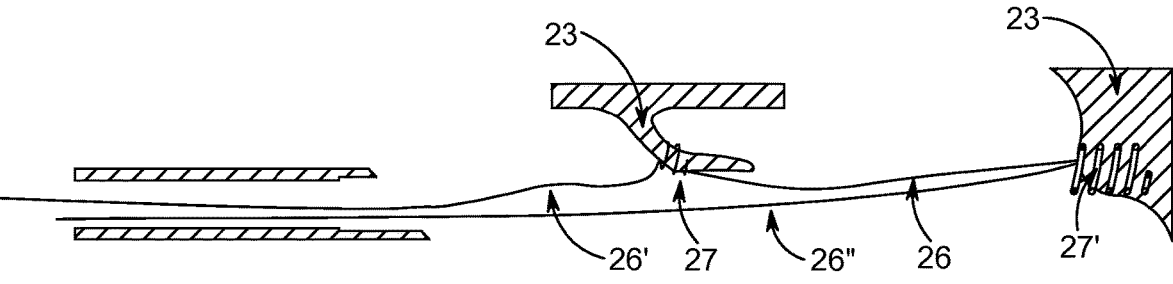

FIG. 11 shows an embodiment of the catheter (2) comprising a mechanism for fixating or anchoring a helical anchor (27) and optionally a suture (26) to a target (23). A distal end section (5) has a distal opening (6) through which tissue (23) is aspirated. In FIG. 11B, the helical anchor (27) is fastened to the tissue (23) by rotating the inner tubular member (45). In FIG. 11C the helical anchor (27) has been fastened to the tissue (23). Since the suture (26) is attached, such as tied, to the helical anchor (27), the suture (26) can be considered to be fastened to the tissue (23).

FIG. 12 shows a further embodiment of the catheter (12) comprising a mechanism for fixating or anchoring a helical anchor (27) and optionally a suture (26) to a target. This embodiment may be particularly useful for, for example, a mitral valve chordal repair. In FIG. 12A, tissue (23) is aspirated through the distal opening (6). A first helical anchor (27) is fastened to the tissue (23). The tissue (first target) may be the papillary muscle. In FIGS. 12 B and C it can be noted that the suture (26) has a first side located in the inner tubular member (45) and a second side returning through a space defined between the inner tubular member (5) and the catheter (2). In this way a second helical anchor (27') can be attached to a second target (23'), which may be leaflet of the mitral valve.

FIG. 13 shows a further embodiment of the presently disclosed negative pressure-based gripping system (1) having an operation unit (46) for operating a tool and/or an inner tubular member inside the catheter (2). The embodiment is similar to the embodiment of FIG. 1 but has an operation unit (46) for inserting an inner tubular member and/or tool in the catheter and operating a tool inside the catheter. Preferably, the (outer) catheter has a remotely operable and flexible distal and is typically connected to the negative pressure, whereas the inner tubular member can be introduced when the distal end of the catheter has been positioned. The inner tubular member with additional functions can then be controlled by the operation unit (46). The embodiment further comprises a feedback light (37) for indicating, based on values from the pressure sensor (9) whether the system has gripped the target after an attempt. There is also a pressure control button (38) for directly activating/deactivating the negative pressure and a positioning control element (36) for positioning the distal end (33). The operation unit (46) may be used to control any function inside the catheter (2), for example, the functions described in FIGS. 5-9 and FIGS. 11-12.

Figure 14:
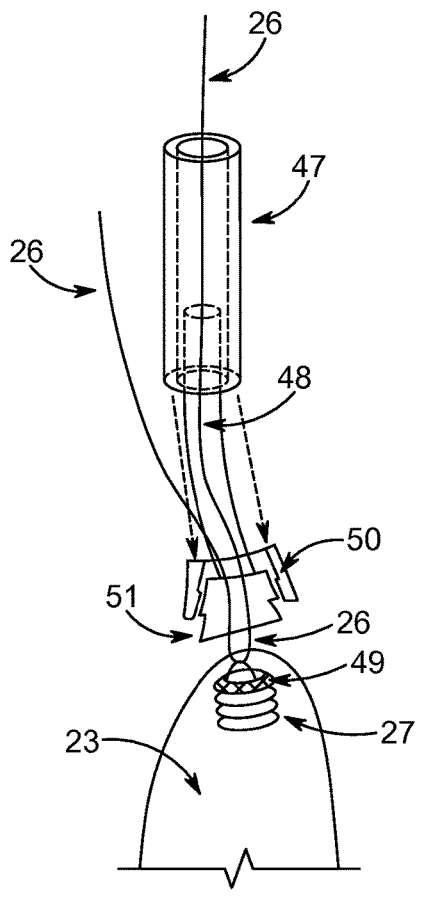
FIG. 14 shows a further embodiment of the catheter with mitral valve chordal repair functionality, wherein the catheter comprises a mechanism for fixating or anchoring a helical anchor and adjusting a tether.

FIG. 14 shows a further embodiment of the catheter with mitral valve chordal repair functionality, wherein the catheter comprises a mechanism for fixating or anchoring a helical anchor and adjusting a tether. The figure illustrates the adjustment and locking of a tether (26). The tether (26) can be adjusted through a snare (48). A helical anchor (27) is attached to a target (23), which may be, for example, a papillary muscle or a leaflet. A mesh cover (49) covers the helical anchor (27) in the fastened position. A lock pusher sheath (47) outside the snare (48) can be pushed along the snare towards the distal end to use first and second lock elements (50, 51) to lock the tether (26) to the helical anchor (27).

Further Details of the Invention

1. A negative pressure-based gripping system for gripping and retaining a target, preferably a moving target, such as a heart or heart tissue of a human or animal, in a fixed position, comprising:
   a catheter having a tubular body; a proximal end; and a remotely operable and flexible distal end section with at least one distal opening;
   a negative pressure generator, such as a vacuum or fluid pump, in connection with the tubular body; and
   a control unit configured to position the distal end of the catheter, wherein said control unit is further configured to control an operation of the negative pressure generator such that a negative pressure is generated in the tubular body to grip the target by the at least one distal opening of the catheter upon positioning of the at least one distal opening adjacent to the target.
2. The negative pressure-based gripping system according to item 1, further comprising at least one pressure sensor for measuring a pressure in the catheter.
3. The negative pressure-based gripping system according to item 2, wherein the at least one pressure sensor is located in the distal end section.
4. The negative pressure-based gripping system according to any of items 2-3, wherein the control unit is further configured to control the operation such that the negative pressure is disconnected or disabled if the measured pressure in the flexible catheter does not remain below a predetermined pressure threshold for a predetermined period of time.
5. The negative pressure-based gripping system according to any of the preceding items, wherein the system is configured to retain the target in a fixed position in relation to the tubular body.
6. The negative pressure-based gripping system according to any of the preceding items, wherein the system is configured to retain at least a portion of a heart in a fixed position over several cardiac cycles.
7. The negative pressure-based gripping system according to any of the preceding items, further comprising a flush container for carrying a fluid suitable for being transferred into the human or animal, said container connected to the tubular body of the flexible catheter.
8. The negative pressure-based gripping system according to item 7, wherein the fluid can be mechanically and/or manually pushed into the tubular body after a gripping and optionally releasing procedure, thereby flushing blood aspirated blood back into the human or animal.
9. The negative pressure-based gripping system according to item 7, wherein the control unit is further configured to control the flush container such that blood aspirated during a gripping procedure is flushed back into the human or animal after a successful or unsuccessful gripping procedure.
10. The negative pressure-based gripping system according to item 9, wherein a flow of fluid from the flush container is controlled by an electrical motor or controlled by a fluid pressure or a gas pressure.
11. The negative pressure-based gripping system according to any of items 1-6, wherein a piston is used as negative pressure generator.
12. The negative pressure-based gripping system according to item 11, wherein the piston is arranged such that a retraction of the piston creates a negative pressure in the tubular body.
13. The negative pressure-based gripping system according to item 12, wherein the piston is further arranged such that a further movement of the piston forward from a retracted position pushes aspirated blood during a gripping procedure back to the human or animal.
14. The negative pressure-based gripping system according to any of items 11-13, wherein the piston is manually or automatically operated.
15. The negative pressure-based gripping system according to any of the preceding items, wherein the remotely operable and flexible distal end section is steerable by means of a computer-assisted control and/or by mechanical control.
16. The negative pressure-based gripping system according to any of the preceding items, wherein the remotely operable and flexible distal end section comprises tendons, cams, rotating wall sections, active materials, pneumatics and/or hydraulics for controlling movement and/or articulation of the distal end, preferably wherein the tendons extend along from the tubular body along the distal end section.
17. The negative pressure-based gripping system according to any of the preceding items, wherein the remotely operable and flexible distal end section can be locked in a rigid configuration.
18. The negative pressure-based gripping system according to items 16-17, wherein the tendons are used to lock the flexible distal end section in the rigid configuration.

19. The negative pressure-based gripping system according to any of the preceding items, the distal end section comprising an end section chamber for further tools arranged to operate on the target.

20. The negative pressure-based gripping system according to any of the preceding items, further comprising a system for tracking the distal end, preferably by imaging modalities such as ultrasound or x-ray based imaging.

21. The negative pressure-based gripping system according to any of the preceding items, wherein the flexible distal end section comprises a marker in the form of a radiopaque section or ultrasound marker, such as an annular, tubular, and/or hollow section around the flexible distal end section, preferably at the distal opening or distal segment.

22. The negative pressure-based gripping system according to any of the preceding items, wherein the catheter is adapted to be introduced in a vein or an artery of the human or animal.

23. The negative pressure-based gripping system according to any of the preceding items, further comprising a wire in the tubular body connected to a contact element arranged at the distal opening, wherein the contact element is configured to transfer energy, such as active radiofrequency energy, to the target, preferably wherein the target is tissue, such as tissue of a heart.

24. The negative pressure-based gripping system according to item 23, wherein the contact element is arranged in the center of the distal opening, and/or wherein the contact element does cover the entire distal opening.

25. The negative pressure-based gripping system according to any of items 23-24, further comprising an energy generator configure to generate energy to the contact element through the wire.

26. The negative pressure-based gripping system according to any of the preceding items, further comprising a puncturing mechanism inside the tubular device, wherein the puncturing mechanism is arranged to puncture tissue, drawn in by generated negative pressure, preferably wherein the puncturing mechanism is remotely operable.

27. The negative pressure-based gripping system according to item 26, wherein the puncturing mechanism comprises a needle.

28. The negative pressure-based gripping system according to item 27, wherein the needle is controlled by a wire or wherein the needle is controlled by fluid in a channel through the tubular body, wherein a pressure in the channel controls backwards and forwards movement of the needle.

29. The negative pressure-based gripping system according to any of the preceding items, further comprising a remotely operable hollow needle at the distal opening for injecting a substance to the target.

30. The negative pressure-based gripping system according to item 29, wherein the hollow needle is connected to a chamber comprising the substance to be injected.

31. The negative pressure-based gripping system according to item 30, wherein the hollow needle and the chamber are controlled by a wire or by a through the tubular body or by a channel comprising fluid and a plunger.

32. The negative pressure-based gripping system according to item 31, wherein forwards movement of the hollow needle and plunger are controlled in two steps, where the hollow needle is moved forward in a first step and the plunger is moved forward in a second step, thereby injecting the substance.

33. The negative pressure-based gripping system according to any of the preceding items, further comprising an inner tubular member.

34. The negative pressure-based gripping system according to item 33, wherein the inner tubular member can be inserted through the proximal end of the catheter.

35. The negative pressure-based gripping system according to any of the preceding items, further comprising an operation unit configured for holding an inner tubular member and/or for operating a tool or function inside the catheter or protruding from the catheter.

36. The negative pressure-based gripping system according to item 33, wherein the inner tubular member is a snare.

37. The negative pressure-based gripping system according to item 36, further comprising a lock pusher sheath outside the snare, wherein the lock pusher sheath can be pushed along the snare to lock a suture relative to a fastening mechanism.

38. The negative pressure-based gripping system according to any of the preceding items, further comprising a stapling or fastening mechanism at the distal opening.

39. The negative pressure-based gripping system according to item 38, wherein the stapling or fastening mechanism comprises a first stapling part and a second stapling part arranged on opposite sides of the distal opening, wherein tissue drawn in through the distal opening is staple by moving the first stapling part and the second stapling part towards each other and driving a metal staple or a thread through the tissue.

40. The negative pressure-based gripping system according to item 38, wherein the stapling or fastening mechanism comprises a helical anchor.

41. The negative pressure-based gripping system according to any of items 38-39, further comprising a suture attached to the fastening mechanism.

42. The negative pressure-based gripping system according to item 41 and 33, wherein the suture comprises a first side arranged in the inner tubular member, and a second side arranged outside the inner tubular member.

43. The negative pressure-based gripping system according to any of the preceding items, further comprising a gripping and/or cutting mechanism at the distal opening, wherein the mechanism comprises a first gripping/cutting part and a second gripping/cutting part arranged on opposite sides of the distal opening, wherein tissue drawn in through the distal opening is gripped/cut by moving the first gripping/cutting part and the second gripping/cutting part towards each other.

44. The negative pressure-based gripping system according to any of the preceding items, further comprising a mechanism for remotely anchoring surgical sutures in tissue drawn by the negative pressure.

45. A method for gripping and retaining a target, preferably a moving target, such as a heart or heart tissue of a human or animal, in a fixed position in relation to at least a part of a device, comprising the steps of:
   providing a device having a catheter having a tubular body; a proximal end; and a remotely operable and flexible end section with a distal opening;
   positioning the distal opening adjacent to the target by steering the distal end remotely;
   generating a negative pressure in the tubular body;
   measuring the pressure in the tubular body for a pre-defined period of time;

if the measured pressure remains below a predefined pressure threshold for longer than a predefined period of time, maintaining the negative pressure in the tubular body to retain the target, otherwise disabling the negative pressure.

46. The method for gripping and retaining a target according to item 45, further comprising the step of flushing the tubular body with a fluid suitable for being transferred into the human or animal towards the distal end of the device, thereby flushing blood back into the human or animal upon a successful or unsuccessful gripping and retaining procedure.

47. The method for gripping and retaining a target according to item 45, further comprising the step of pushing aspirated blood back into the human or animal upon a successful or unsuccessful gripping and retaining procedure.

48. The method for gripping and retaining a target according to any of items 45-47, using the system of any of items 1-44.

49. The method for gripping and retaining a target according to any of items 45-48, further comprising the step of providing therapy, treatment or surgery to the target.

50. The method for gripping and retaining a target according to any of items 45-49, further comprising the step of introducing the device by a vein or an artery of the human or animal before positioning the distal opening.

51. The method for gripping and retaining a target according to any of items 45-50, further comprising the step of applying energy to the mitral annulus of a heart through a contact element arranged at the distal opening.

52. The method for gripping and retaining a target according to any of items 45-51, further comprising the step of stapling a valve part of the mitral valve having a prolapse by using a stapling mechanism at the distal opening.

53. The method for gripping and retaining a target according to any of items 45-52, further comprising the step of anchoring or attaching a medical component to the target.

54. The method for gripping and retaining a target according to any of items 45-53, further comprising the step of puncturing the target by using a puncturing mechanism inside the tubular device at the distal opening.

55. The method for gripping and retaining a target according to item 54, wherein the puncturing mechanism is a hollow needle, further comprising the step of injecting a substance into the target through the hollow needle.

56. A method for performing mitral valve chordal repair of a heart, comprising the steps of:

providing a device having a catheter having a tubular body; a proximal end; and a remotely operable and flexible end section with a distal opening;

introducing the device in the femoral or jugular vein;

positioning the distal opening adjacent to the target by steering the distal end remotely;

using a guidewire to enter a right atrium of the heart;

puncturing an atrial septum and crossing the atrial septum of the heart;

locating, such as by ultrasound, the device so that the end is located on a papillary muscle generating a negative pressure in the tubular body, thereby locking the distal opening to a papillary muscle of the heart;

fixating a suture, such as by anchoring a helical anchor, in the papillary muscle;

releasing the negative pressure and moving the device to the leaflet of the mitral valve that has a ruptured chordae;

generating a negative pressure in the tubular body, thereby locking the distal opening to the leaflet of the mitral valve;

fixating a suture, such as by anchoring a helical anchor, in the leaflet;

adjusting the length of the two sutures so that the valve becomes competent.

57. An apparatus or a medical instrument for performing mitral valve chordal repair of a heart comprising the negative pressure-based gripping system according to any of items 1-44.

58. The apparatus according to item 57 configured to perform the method according to item 56.

59. An injection device comprising the negative pressure-based gripping system according to any of items 29-32.

60. A suture fastening device comprising the negative pressure-based gripping system according to any of items 38-41.

The invention claimed is:

1. A negative pressure-based gripping system for gripping and retaining a target, preferably a moving target, in a fixed position, comprising:

a catheter having a tubular body; a proximal end; and a remotely operable and flexible distal end section with at least one distal opening;

a negative pressure generator in connection with the tubular body configured to generate a negative pressure in the tubular body to grip the target by the at least one distal opening of the catheter upon positioning of the at least one distal opening adjacent to the target; and a control unit comprising a processor that is configured to position the distal end of the catheter, wherein said control unit is further configured to control an operation of the negative pressure generator to automatically disconnect or disable the negative pressure if a measured pressure in the tubular body does not exceed a predetermined pressure threshold for a predetermined period of time.

2. The negative pressure-based gripping system according to claim 1, further comprising at least one pressure sensor for measuring a pressure in the catheter.

3. The negative pressure-based gripping system according to claim 1, wherein the system is configured to retain the target in a fixed position in relation to the tubular body.

4. The negative pressure-based gripping system according to claim 1, wherein the system is configured to retain at least a portion of a heart in a fixed position over several cardiac cycles.

5. The negative pressure-based gripping system according to claim 1, further comprising a flush container for carrying a fluid suitable for being transferred into the human or animal, said container connected to the tubular body of the flexible catheter.

6. The negative pressure-based gripping system according to claim 5, wherein said system is configured such that the fluid can be mechanically and/or manually pushed into the tubular body after a gripping and releasing procedure, thereby flushing blood aspirated blood back into the human or animal.

7. The negative pressure-based gripping system according to claim 5, wherein the control unit is further configured to control the flush container such that blood aspirated during a gripping procedure is flushed back into the human or animal after a successful or unsuccessful gripping procedure.

8. The negative pressure-based gripping system according to claim 1, the distal end section comprising an end section chamber for further tools arranged to operate on the target.

9. The negative pressure-based gripping system according to claim 1, further comprising a puncturing mechanism inside the tubular device, wherein the puncturing mechanism is arranged to puncture tissue, drawn in by generated negative pressure, wherein the puncturing mechanism is remotely operable.

10. The negative pressure-based gripping system according to claim 1, further comprising an inner tubular member.

11. The negative pressure-based gripping system according to claim 10, wherein the inner tubular member is adapted to be inserted through the proximal end of the catheter.

12. The negative pressure-based gripping system according to claim 10, wherein the inner tubular member is a snare and wherein the negative pressure-based gripping system further comprises a lock pusher sheath outside the snare, wherein the lock pusher sheath can be pushed along the snare to lock a suture relative to a fastening mechanism.

13. The negative pressure-based gripping system according to claim 1, further comprising an operation unit configured for holding an inner tubular member and/or for operating a tool or function inside the catheter or protruding from the catheter.

14. The negative pressure-based gripping system according to claim 1, further comprising a stapling or fastening mechanism at the distal opening.

15. The negative pressure-based gripping system according to claim 14, wherein the stapling or fastening mechanism comprises a helical anchor and/or further comprising a suture attached to the fastening mechanism.

16. The negative pressure-based gripping system according to claim 15, wherein the suture comprises a first side arranged in the inner tubular member, and a second side arranged outside the inner tubular member.

17. The negative pressure-based gripping system according to claim 1, wherein the control unit is configured to disconnect or disable the negative pressure via a valve arranged between the negative pressure generator and the tubular body.

18. A method for gripping and retaining a target, preferably a moving target, in a fixed position in relation to at least a part of a device, comprising the steps of:

providing a device having a catheter having a tubular body; a proximal end; and a remotely operable and flexible end section with a distal opening;

positioning the distal opening adjacent to the target by steering the distal end remotely;

generating a negative pressure in the tubular body to grip the target by the distal opening of the catheter upon positioning of the at least one distal opening adjacent to the target;

measuring the pressure in the tubular body for a predefined period of time;

maintaining the negative pressure in the tubular body to retain the target;

detecting whether the measure pressured has exceeded a predefined pressure threshold for longer than a predefined period of time; and disabling the negative pressure based on the detection.

19. A method for performing a surgical process to a target in the form of a heart, comprising the steps of:

a) inserting, transfemorally, a device having a catheter having a tubular body; a proximal end; and a remotely operable and flexible end section with a distal opening;

b) positioning the distal opening of the device adjacent to the target by steering the distal end remotely;

c) generating a negative pressure in the tubular body to grip the target by the distal opening of the catheter upon positioning of the at least one distal opening adjacent to the target;

d) measuring the pressure in the tubular body for a predefined period of time;

e) detecting whether the pressure exceeds a predefined pressure threshold for longer than the predetermined amount of time;

f) disabling the negative pressure based on the detection;

g) repeating steps c) through f) until the target is retained; and h) performing the surgical process through the tubular body of the catheter.

20. A method for performing mitral valve chordal repair of a heart, comprising the steps of:

providing a device having a catheter having a tubular body; a proximal end; and a remotely operable and flexible end section with a distal opening;

introducing the device in a femoral or jugular vein;

positioning the distal opening adjacent to the target by steering the distal end remotely;

using a guidewire to enter a right atrium of the heart;

puncturing an atrial septum and crossing the atrial septum of the heart;

locating the device so that the end is located on a papillary muscle;

generating a negative pressure in the tubular body to grip the distal opening to a papillary muscle of the heart;

measuring the pressure in the tubular body for a first predefined period of time;

detecting, in a first detection step, whether the pressure exceeds a first predefined pressure threshold for longer than the first predetermined amount of time;

disabling the negative pressure based on the first detection;

fixating a suture in the papillary muscle;

releasing the negative pressure and moving the device to the leaflet of the mitral valve that has a ruptured chordae;

generating a negative pressure in the tubular body to grip the distal opening to the leaflet of the mitral valve;

measuring the pressure in the tubular body for a second predefined period of time;

detecting, in a second detection step, whether the pressure exceeds a second predefined pressure threshold for longer than the second predetermined amount of time;

disabling the negative pressure based on the second detection;

fixating a suture in the leaflet; and adjusting the length of the two sutures so that the valve becomes competent.

* * * * *